United States Patent
Morales

(10) Patent No.: US 9,517,306 B2
(45) Date of Patent: Dec. 13, 2016

(54) METHOD AND SYSTEM FOR CLOSED-LOOP CONTROL OF AN ARTIFICIAL PANCREAS

(71) Applicant: Animas Corporation, West Chester, PA (US)

(72) Inventor: Carlos Morales, West Chester, PA (US)

(73) Assignee: ANIMAS CORPORATION, West Chester, PA (US)

( * ) Notice: Subject to any disclaimer, the term of this patent is extended or adjusted under 35 U.S.C. 154(b) by 894 days.

(21) Appl. No.: 13/840,429

(22) Filed: Mar. 15, 2013

(65) Prior Publication Data

US 2014/0276555 A1 Sep. 18, 2014

(51) Int. Cl.
  *G06F 19/00* (2011.01)
  *A61M 5/172* (2006.01)
  *A61M 5/178* (2006.01)

(52) U.S. Cl.
  CPC .... *A61M 5/1782* (2013.01); *A61M 2205/3569* (2013.01); *G06F 19/3468* (2013.01)

(58) Field of Classification Search
  None
  See application file for complete search history.

(56) References Cited

U.S. PATENT DOCUMENTS

| | | | |
|---|---|---|---|
| 6,922,819 B2 | 7/2005 | Visweswariah | |
| 7,060,059 B2 | 6/2006 | Keith et al. | |
| 7,276,029 B2 | 10/2007 | Goode, Jr. et al. | |
| 8,062,249 B2 | 11/2011 | Wilinska et al. | |
| 2009/0031260 A1 | 1/2009 | Angyal et al. | |
| 2010/0160778 A1 | 6/2010 | Eskandari et al. | |
| 2011/0208156 A1 | 8/2011 | Doyle, III et al. | |
| 2011/0257627 A1 | 10/2011 | Hovorka | |
| 2011/0276025 A1* | 11/2011 | Wu | A61M 5/14276 604/504 |
| 2011/0307438 A1 | 12/2011 | Fernandez | |
| 2011/0313680 A1 | 12/2011 | Doyle, III et al. | |

FOREIGN PATENT DOCUMENTS

WO   WO-2012051344 A2   4/2012

OTHER PUBLICATIONS

Grosman, Benyamin, Ph.D. et al, "Zone Model Predictive Control: A Strategy to Minimize Hyper and Hypoglycemic Events" Journal of Diabetes Science and Technology, vol. 4, Issue 4, Jul. 2010 (15 pgs.).
Gillis, Rachel et al., "Glucose Estimation and Prediction through Meal Responses Using Ambulatory Subject Data for Advisory Mode Model Predictive Control", Journal of Diabetes Science and Technology, vol. 1, Issue 6, Nov. 2007 (9 pgs.).
Wang, Youqing et al., "Closed-Loop Control of Artificial Pancreatic β-Cell in Type 1 Diabetes Mellitus Using Model Predictive Iterative Learning Control" IEEE Transactions on Biomedical Engineering, vol. 57, No. 2, Feb. 2010 (9 pgs.).
Percival et al., in "Closed-Loop Control and Advisory Mode Evaluation of an Artificial Pancreatic β Cell: Use of Proportional-Integral-Derivative Equivalent Model-Based Controllers" Journal of Diabetes Science and Technology, vol. 2, Issue 4, Jul. 2008 (9 pgs.).
Soru, Paola et al., "MPC Based Artificial Pancreas; Strategies for Individualization and Meal Compensation" Annual Reviews in Control 36, p. 118-128 (2012) (11 pgs.).
Cobelli et al., "Artificial Pancreas: Past, Present, Future", Perspectives in Diabetes, vol. 60, Nov. 2011 (11 pgs.).
Magni et al., "Run-to-Run Tuning of Model Predictive Control for Type 1 Diabetes Subjects: In Silico Trial" Journal of Diabetes Science and Technology, vol. 3, Issue 5, Sep. 2009 (8 pgs.).
Lee et al., "A Closed-Loop Artificial Pancreas Using Model Predictive Control and a Sliding Meal Size Estimator" Journal of Diabetes Science and Technology, vol. 3, Issue 5, Sep. 2009 (9 pgs.).
Lee et al., "A Closed-Loop Artificial Pancreas based on MPC: Human Friendly Identification and Automatic Meal Disturbance Rejection" Proceedings of the 17th World Congress, The International Federation of Automatic Control, Seoul Korea Jul. 6-11, 2008; (6 pgs.).
Magni et al., "Model Predictive Control of Type 1 Diabetes: An in Silico Trial" Journal of Diabetes Science and Technology, vol. 1, Issue 6, Nov. 2007 (9 pgs.).
Wang et al., "Automatic Bolus and Adaptive Basal Algorithm for the Artificial Pancreatic β-Cell" Diabetes Technology and Therapeutics, vol. 12, No. 11, 2010 (10 pgs.).
Percival, Matthew W. et al., "Closed-Loop Control of an Artificial Pancreatic β-Cell Using Multi-Parametric Model Predictive Control" Department of Chemical Engineering, Univ of California, Santa Barbara, Sansum Diabetes Research Institute (11 pgs.).
Geyer, Charles J., "Non-linear Optimization", found at http://www.stat.umn.edu/geyer/trust/library/trust/html/trust.html (6 pgs.).
Cliff, E.M., "Trust-Region Methods", AOE 5244, from From http://www.dept.aoe.vt.edu/~cliff/aoe5244_99/week_4_d.pdf (18 pages).

(Continued)

*Primary Examiner* — Anna Skibinsky
(74) *Attorney, Agent, or Firm* — Barclay Damon, LLP

(57) ABSTRACT

A local extremum of a function $f$ is determined by computing a Jacobian of $f$ at a test point x by adding an imaginary part to x and a Hessian of $f$ by adding two imaginary parts to a multicomplex copy of x and extracting a third imaginary part. Solving a system of equations defined by the Jacobian and Hessian yields a delta; the process is repeated until convergence. This method is used in each of a series of time intervals to compute an insulin-delivery amount for an insulin pump. $f$ is a model-predictive-control cost function; x is a set of successive candidate insulin delivery amounts beginning from a selected time interval. A system includes a glucose monitor and a controller using glucose measurement data therefrom to determine an insulin delivery amount for a time interval by minimizing $f$; an insulin pump provides insulin corresponding to the delivery amount.

13 Claims, 12 Drawing Sheets

(56) References Cited

OTHER PUBLICATIONS

Wang, Baohua, Optimization of Circuit Trajectories: an Auxiliary Network Approach, 0-7803-9451-8/06/$20.00 Copyright 2006, IEEE, pp. 416-421 (6 pgs.).

Visweswariah, Chandu, "Dynamic Tuning for High-Performance Custom Digital Design," IBM Thomas J. Watson Research Center, Yorktown Heights, NY 10598, of 77.1 (77 pgs.).

* cited by examiner

METHOD AND SYSTEM FOR CLOSED-LOOP CONTROL OF AN ARTIFICIAL PANCREAS

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic agents such as insulin have commonly been administered as multiple daily injections of a mixture of rapid- and intermediate-acting drugs via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of drug delivery devices that relieve the patient of the need for syringes or drug pens and the need to administer multiple daily injections. The drug delivery device allows for the delivery of a drug in a manner that bears greater similarity to the naturally occurring physiological processes and can be controlled to follow standard or individually-modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body, and are generally controlled via a user interface built in to the device or arranged on a separate remote device.

Blood or interstitial glucose monitoring is required to achieve acceptable glycemic control. For example, delivery of suitable amounts of insulin by the drug delivery device requires that the patient frequently determine his or her blood glucose level and manually input this value into a user interface for the external pumps. The user interface or a corresponding controller then calculates a suitable modification to the default or currently in-use insulin delivery protocol, i.e., dosage and timing, and subsequently communicates with the drug delivery device to adjust its operation accordingly. The determination of blood glucose concentration is typically performed by means of an episodic measuring device such as a hand-held electronic meter which receives blood samples via enzyme-based test strips and calculates the blood glucose value based on the enzymatic reaction. Throughout this disclosure, the terms "patient," "subject," and "user" (i.e., user of a drug delivery device) are used interchangeably.

Continuous glucose monitoring (CGM) has also been utilized over the last twenty years with drug delivery devices to allow for closed loop control of the insulin(s) being infused into the diabetic patients. To allow for closed-loop control of the infused insulins, proportional-integral-derivative ("PID") controllers have been utilized with mathematical model of the metabolic interactions between glucose and insulin in a person. The PID controllers can be tuned based on simple rules of the metabolic models. However, glucose measurements in the body show significant variability due to frequent changes in the glucose level and variability in the measurement instruments. When the PID controllers are tuned or configured to aggressively regulate the blood glucose levels of a subject, overshooting of the set level can occur, which is often followed by oscillations, which is highly undesirable in the context of regulation of blood glucose. Model predictive controllers ("MPC") have also been used. The MPC controller has been demonstrated to be more robust than PID because MPC considers the near future effects of control changes and constraints in determining the output of the MPC, whereas PID typically involves only past outputs in determining future changes. MPC therefore is more effective than PID in view of the complex interplay between insulin, glucagon, and blood glucose. Constraints can be implemented in the MPC controller such that MPC prevents the system from running away when a control limit has been reached. For example, some schemes do not deliver any glucose during a hypoglycemic excursion. Another benefit of MPC controllers is that the model in the MPC can, in some cases, theoretically compensate for dynamic system changes whereas a feedback control, such as PID control, such dynamic compensation would not be possible.

Additional details of the MPC controllers, variations on the MPC and mathematical models representing the complex interaction of glucose and insulin are shown and described in the following documents:

U.S. Pat. No. 7,060,059; US Patent Application Nos. 2011/0313680 and 2011/0257627; International Publication WO 2012/051344;

Percival et al., "Closed-Loop Control and Advisory Mode Evaluation of an Artificial Pancreatic β Cell: Use of Proportional-Integral-Derivative Equivalent Model-Based Controllers" Journal of Diabetes Science and Technology, Vol. 2, Issue 4, July 2008.

Paola Soru et al., "MPC Based Artificial Pancreas; Strategies for Individualization and Meal Compensation" Annual Reviews in Control 36, p. 118-128 (2012), Cobelli et al., "*Artificial Pancreas: Past, Present, Future*" Diabetes Vol. 60, November 2011;

Magni et al., "*Run-to-Run Tuning of Model Predictive Control for Type 1 Diabetes Subjects: In Silico Trial*" Journal of Diabetes Science and Technology, Vol. 3, Issue 5, September 2009.

Lee et al., "A Closed-Loop Artificial Pancreas Using Model Predictive Control and a Sliding Meal Size Estimator" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the 17$^{th}$ World Congress, The International Federation of Automatic Control, Seoul Korea Jul. 6-11, 2008;

Magni et al., "*Model Predictive Control of Type 1 Diabetes: An in Silico Trial*" Journal of Diabetes Science and Technology, Vol. 1, Issue 6, November 2007;

Wang et al., "Automatic Bolus and Adaptive Basal Algorithm for the Artificial Pancreatic β-Cell" Diabetes Technology and Therapeutics, Vol. 12, No. 11, 2010; and Percival et al., "Closed-Loop Control of an Artificial Pancreatic β-Cell Using Multi-Parametric Model Predictive Control" Diabetes Research 2008.

All articles or documents cited in this application are hereby incorporated by reference into this application as if fully set forth herein.

Drug delivery devices generally provide insulin at a "basal rate," i.e., provide a certain amount of insulin every few minutes in a pre-programmed, daily pattern. Some drug delivery devices also permit the user to specify a "temporary basal," in which the normal daily cycle is altered for a selected length of time. Some drug delivery devices permit the user to manually request that a "bolus," a specified amount of insulin, be delivered at a specified time. For example, before a meal, the user can request a bolus of additional insulin be delivered to process the glucose produced by digestion of the meal. Some drug delivery devices permit the specified amount to be delivered over a period of time rather than all at once; time-extended delivery is referred to as an "extended bolus."

The term "continuous" is convenient but not strictly accurate. In practice, CGM generally samples glucose on a regular time scale, e.g., once per five minutes. MPC updates are performed, e.g., in the time intervals between glucose measurements. In order for continuous glucose monitoring to be as useful as possible, it is desirable to reduce the length of time intervals to provide more frequent control of glucose level. However, CGM and MPC systems usable by subjects outside a laboratory setting, e.g., in daily live, are generally small, battery-powered systems without the space, cooling, or energy density to support high-speed, expensive microprocessors. There is, therefore, a need of a way of more efficiently performing MPC computations that can be implemented on low-powered portable or mobile electronic devices, e.g., handheld glucose meter/controller units such as the ONETOUCH PING from JOHNSON & JOHNSON.

SUMMARY OF THE DISCLOSURE

A significant portion of the time required to compute an MPC update is in performing the mathematical minimization of the cost function. In MPC, the cost function takes as input a vector of candidate insulin delivery amounts for the next M time intervals. The cost function returns an estimated cost of actually delivering the candidate insulin delivery amounts. The cost function is thus, e.g., $\mathbb{R}^5 \to \mathbb{R}$. To determine the insulin to deliver in a given time interval, the cost function is minimized and the first element of the resulting input vector is used as the insulin delivery amount. At the next time interval, the minimization process is repeated to determine the next insulin delivery amount. The cost function includes a computation of estimated blood glucose based on the input insulin amounts.

Various techniques are known in the art for performing mathematical optimization. For example, US 2009/0031260 A1 discloses a semiconductor-process optimization system that uses sensitivities of electrical metrics with respect to small variations in the input process parameters to guide optimization. Sensitivities are computed by field solvers. This is computationally very expensive and not suitable for real-time use, and in fact this scheme is directed to an interactive design tool for semiconductor process engineers to use, not a real-time optimization system.

Many optimization schemes use Jacobian and Hessian matrices in determining a step from one input to the function to a nearby input that results in a value of the function closer to the desired optimization condition. US 2010/0057222 A1 describes computing gradients and Hessians in systems using neural networks. However, this is limited to neural networks and is not applicable to pre-programmed systems (as opposed to error-propagation-based learning systems).

U.S. Pat. No. 6,922,819 and "Dynamic Tuning for High-Performance Custom Digital Design" (Visweswariah, ICCAD 1996) describe computing gradients by direct, adjoint, or all-at-once adjoint methods. However, both the direct and adjoint methods require transformation of equations representing the system. The direct method requires differentiating the transformed equations, and solving the resulting differentiated system. Moreover, it can require additional interpolation steps or conservative time scales to obtain useful results. Furthermore, transformation of the equations of the glucose model can be very complex. The glucose model is a time series over a limited horizon, and any transformed equation not over a limited horizon can require more memory than available. It is therefore desirable to provide a control algorithm that does not require transforming the equations describing the system.

US 2011/0307438 A1 describes conventional ways of computing Jacobians and Hessians by perturbing the input of the cost function slightly, and subtracting and dividing. For example, the computation of Hessians is described in para. [0176] and Eq. 89 of this reference. A small value ε is added to one of the inputs of the function or its derivative, and the difference between the function (derivative) values at the point after adding ε and at the point before adding ε is divided by ε to estimate the Jacobian (Hessian). This technique is based on the definition of the derivative, e.g., the first derivative $f'(x)$ of $f$ at x:

$$f'(x) = \frac{\partial f}{\partial x_i} = \lim_{\varepsilon \to 0} \frac{f(x+\varepsilon) - f(x)}{\varepsilon}$$

However, when performing successive numerical differentiation of nonlinear functions, loss of precision can reduce the correctness of the results. When finite difference approximations to the analytical derivative are computed using numerical methods, e.g., as in the schemes described above, errors can be introduced into the computation. Introduced errors can be due to floating point truncation or due to floating point round-off. In general, the numerator of the fraction above will likely be very small, of the same order of magnitude as ε. Therefore, small values of ε will result in dividing a near-zero number by another near-zero number, a situation in which the differences between computer floating-point numbers (e.g., IEEE-754) and the real numbers can become evident.

Specifically, the fraction above is called the forward difference approximation to the gradient. These values are computed using a finite-resolution digital approximation. So, a very small but non-zero value of $\epsilon$ may be used to compute these results. This value can be linked to the machine precision, e.g., can be the smallest value of the floating point number that can be represented in a particular microprocessor, below which all values will be truncated to zero. For the form outlined above, the error in computing the derivative using a nonzero $\epsilon$ is proportional to $\epsilon$. This error is called truncation error. Truncation error reduces as $\epsilon$ reduces.

However, as $\epsilon$ is reduced, round-off error is introduced. This error is made evident when two nearly equal quantities are subtracted (e.g., $f(x+\epsilon)-f(x)$) and the difference is divided by a very small quantity ($\epsilon$). Since all the intermediate quantities ($f(x)$, $f(x+\epsilon)$, $\epsilon$) are quantized to the set of numbers the computer can represent in floating point, the smaller those quantities, the larger the quantization error is, percentage-wise. Round-off error is therefore more significant for small values of $\epsilon$ than for large values of $\epsilon$. Accordingly, the scheme of '438 and similar schemes cannot achieve less than a certain amount of error in computations of, or involving, Jacobians or Hessians.

A previously unrecognized problem with conventional optimization schemes is that they are limited to operation in the domains $\mathbb{R}^n$ of real numbers. In contrast, the present application advantageously makes use of complex and bicomplex spaces $\mathbb{C}_1^n$ and $\mathbb{C}_2^n$ where $\mathbb{C}_0^n \stackrel{\text{def}}{=} (\mathbb{C}_0)^n \stackrel{\text{def}}{=} \mathbb{R}^n$ and likewise for other superscripts and subscripts. These approaches reduce the error contributed via floating point round-off, permitting smaller values of $\epsilon$ to be used, thereby reducing truncation error. This permits more accurate derivative calculation. Moreover, various aspects described herein do not use the subtraction operation, which permits faster computation of Jacobians and Hessians and thus faster optimization runs.

By using these approaches we can replace some conventional algorithms such as Richardson extrapolation and N-point stencil, which attempt to avoid round-off by evaluating the cost function many more times than necessary. These schemes, by running longer, drain more power (reducing battery life) and take more time (reducing responsiveness). They are, therefore, not preferred for portable insulin monitors.

In one aspect, therefore, we have devised a method of determining a local extremum of a function on an n-dimensional space. The method can be achieved by automatically performing the following steps using a controller:

selecting a value for a real-type test point in the n-dimensional space;

computing an approximate Jacobian of the function at the test point by, for each dimension i of the n dimensions:
setting a complex-type computation point c equal to the test point;
setting an imaginary part of element i of c equal to a nonzero increment;
computing a complex-type value of the function at c; and
dividing the imaginary part of the complex-type computed function value by the increment to form element i of the Jacobian;

computing an approximate Hessian of the function at the test point by, for each pair of dimensions (i,j), each i and j one of the n dimensions:
setting a multicomplex-type computation point b equal to the test point;
setting a first imaginary part of element i of b equal to a nonzero first increment;
setting a second imaginary part of element j of b equal to a nonzero second increment;
computing a multicomplex-type value of the function at b; and
dividing the third imaginary part of the computed multicomplex-type function value by the product of the first and second increments to form element (i,j) of the Hessian;

solving a system of equations defined by the approximate Hessian and the approximate Jacobian to find a delta;

modifying the test point according to the delta to form a next point;

determining whether the next point satisfies selected convergence criteria; and if not, assigning the value of the next point to the test point and repeating the computing steps and the solving through the determining step.

In another aspect, we have devised apparatus for the delivery of insulin. The apparatus may include the following components:

a) a glucose monitor adapted to measure respective glucose levels of a subject at discrete time intervals and provide respective glucose measurement data indicating each measured glucose level;

b) an insulin infusion pump configured to deliver insulin in response to a delivery control signal;

c) a memory configured to store a plurality of basal insulin delivery amounts at respective ones of the discrete time intervals; and d) a model predictive controller adapted to, for each of a plurality of the discrete time intervals:
i) receive the glucose measurement data for that time interval from the glucose monitor;
ii) determine an insulin delivery amount for that time interval using model predictive control based on a selected target glucose concentration range, the received glucose measurement data, the stored basal insulin delivery profile amounts for that time interval and n−1 successive time intervals; and
iii) provide to the insulin infusion pump a delivery control signal corresponding to the determined insulin delivery amount, so that a corresponding amount of insulin is delivered;

e) in which the model predictive controller is adapted to determine the insulin delivery amount by mathematical minimization of a cost function that computes a cost metric correlated with physiological-fluid glucose-level excursions from a selected target glucose range for a particular set of n successive candidate insulin delivery amounts beginning from the selected one of the time intervals, and the model predictive controller, in order to carry out the mathematical minimization, is adapted to:
i) select n candidate insulin delivery values for a real-type n-dimensional test point;
ii) for each dimension i of the n dimensions:
A) set a complex-type n-dimensional computation point c equal to the test point;
B) set an imaginary part of element i of c equal to a nonzero increment;

C) compute a complex-type value of the cost function at c; and

D) divide the imaginary part of the complex-type computed function value by the increment to form element i of an approximate Jacobian of the function at the test point;

iii) for each pair of dimensions (i,j), each i and j one of the n dimensions:

A) set a multicomplex-type n-dimensional computation point b equal to the test point;

B) set a first imaginary part of element i of b equal to a nonzero first increment;

C) set a second imaginary part of element j of b equal to a nonzero second increment;

D) compute a multicomplex-type value of the cost function at b; and

E) divide the third imaginary part of the computed multicomplex-type function value by the product of the first and second increments to form element (i,j) of an approximate Hessian of the function at the test point;

iv) solve a system of equations defined by the approximate Hessian and the approximate Jacobian to find a delta;

v) modify the test point according to the delta to form a next point;

vi) determine whether the next point satisfies selected convergence criteria;

vii) if not, assign the value of the next point to the test point and repeat the computation of the approximate Jacobian and Hessian of the function, solution of the system of equations, modification of the test point, and determination of whether the next point satisfies the selected convergence criteria; and viii) if so, select the first element of the next point as the candidate insulin delivery amount for the selected one of the time intervals;

f) and further in which the model predictive controller is adapted to, in order to compute the cost function for each input set of n successive candidate insulin delivery amounts:

i) predict an excursion of the glucose level from a selected target glucose range using at least some of the glucose measurements, a glucose-insulin dynamic model of the subject, and an input set of n candidate insulin delivery amounts;

ii) compute a deviation of the candidate insulin delivery amounts from respective selected basal delivery amounts; and iii) form a weighted sum of respective values representing the predicted excursion and the computed deviation using respective selected weights, such that the output of the cost function includes the weighted sum.

In another aspect, we have devised a method to control an infusion pump responsive to a controller that receives data from a glucose sensor. The method can be achieved measuring respective glucose levels of a physiological fluid from a subject for each time interval of a series of discrete time intervals using the glucose sensor and automatically performing the following steps using a controller:

automatically calculating an insulin delivery amount for a selected one of the time intervals by mathematically minimizing a cost function that computes a cost metric correlated with physiological-fluid glucose-level excursions from a selected target glucose range for a particular set of n successive candidate insulin delivery amounts beginning from the selected one of the time intervals, the minimizing including:

selecting n candidate insulin delivery values for a real-type n-dimensional test point;

computing an approximate Jacobian of the cost function at the test point by evaluating the cost function, in which the model predictive controller computes the cost function for each input set of n successive candidate insulin delivery amounts by:

predicting an excursion of the glucose level from a selected target glucose range using at least some of the glucose measurements, a glucose-insulin dynamic model of the subject, and the candidate insulin delivery amounts;

computing a deviation of the candidate insulin delivery amounts from respective selected basal delivery amounts; and forming a weighted sum of respective values representing the predicted excursion and the computed deviation using respective selected weights such that the output of the cost function includes the weighted sum;

computing an approximate Hessian of the cost function at the test point by evaluating the cost function;

solving a system of equations defined by the approximate Hessian and the approximate Jacobian to find a delta;

modifying the test point according to the delta to form a next point;

determining whether the next point satisfies selected convergence criteria;

if not, assigning the value of the next point to the test point and repeating the computing of the approximate Jacobian and Hessian, solving the system of equation, modifying the test point and the determining step; and if so, selecting a first element of the next point as the candidate insulin delivery amount for the selected one of the time intervals;

determining an approved insulin delivery amount from the insulin delivery amount; and commanding the infusion pump to deliver the approved insulin delivery amount to the subject.

These aspects provide improved control over blood glucose level by permitting shorter MPC time intervals to be used. They can also increase battery life of portable devices including model-predictive controllers.

Accordingly, in any of the aspects described earlier, the following features may also be utilized in various combinations with the previously disclosed aspects. For example, the computing-approximate Jacobian step can include, for each dimension i of the n dimensions:

setting a complex-type n-dimensional computation point c equal to the test point;

setting an imaginary part of element i of c equal to a nonzero increment;

computing a complex-type value of the cost function at c; and dividing the imaginary part of the complex-type computed function value by the increment to form element i of the Jacobian; and the computing-approximate-Hessian step can include, for each pair of dimensions (i,j), each i and j one of the n dimensions:

setting a multicomplex-type n-dimensional computation point b equal to the test point;

setting a first imaginary part of element i of b equal to a nonzero first increment;

setting a second imaginary part of element j of b equal to a nonzero second increment;

computing a multicomplex-type value of the cost function at b; and dividing the third imaginary part of the computed multicomplex-type function value by the product of the first and second increments to form element (i,j) of the Hessian.

The extremum can be a minimum and the solving step can include finding a delta that will reduce the value of the function. The selecting step can include receiving the value for the test point via an interface. The system of equations can include Hs=−g for the approximate Hessian H, the approximate Jacobian g, and the delta s. The solving step can include executing at least two iterations of a conjugate-gradient algorithm.

Methods described herein can include selecting a value for a trust region. The modifying step can include computing the next point as the sum of the test point and the delta and clipping the sum within the trust region, and the determining step can includes determining whether the value of the function at the next point is closer to the extremum than the value of the function at the test point; if not, contracting the trust region and determining that the next point does not satisfy the selected convergence criteria; and if so, determining whether the next point satisfies the selected convergence criteria and, if not, expanding the trust region. The clipping step can include determining a local extremum along a line segment extending from the test point in a direction indicated by the computed approximate Jacobian to the boundary of the test region; and determining the clipped sum to be the point at the intersection of the boundary of the trust region with the ray starting at the determined local extremum and extending parallel to the ray from the test point to the next point.

In various aspects, the multicomplex type can be a bicomplex type and the third imaginary part can be a combined imaginary part. The multicomplex type can be a quaternion type, and the first, second, and third imaginary parts can be $i_Q$, $j_Q$, and $k_Q$ parts, respectively.

The model predictive controller of various aspects can further be adapted to predict an excursion of a glucose level of the subject from the selected target glucose range using a safety model and at least some of the glucose measurement data for a plurality of the time intervals; and reduce the determined insulin delivery amount according to the predicted excursion. The glucose monitor can include a plurality of glucose sensors. The determining-approved-amount step can include providing the candidate insulin delivery amount as the approved insulin delivery amount, or reducing the candidate delivery amount according to a safety model to provide the approved insulin delivery amount.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that cause a biological response (e.g., glycemic response) in the body of a user or patient.

Figure 1:
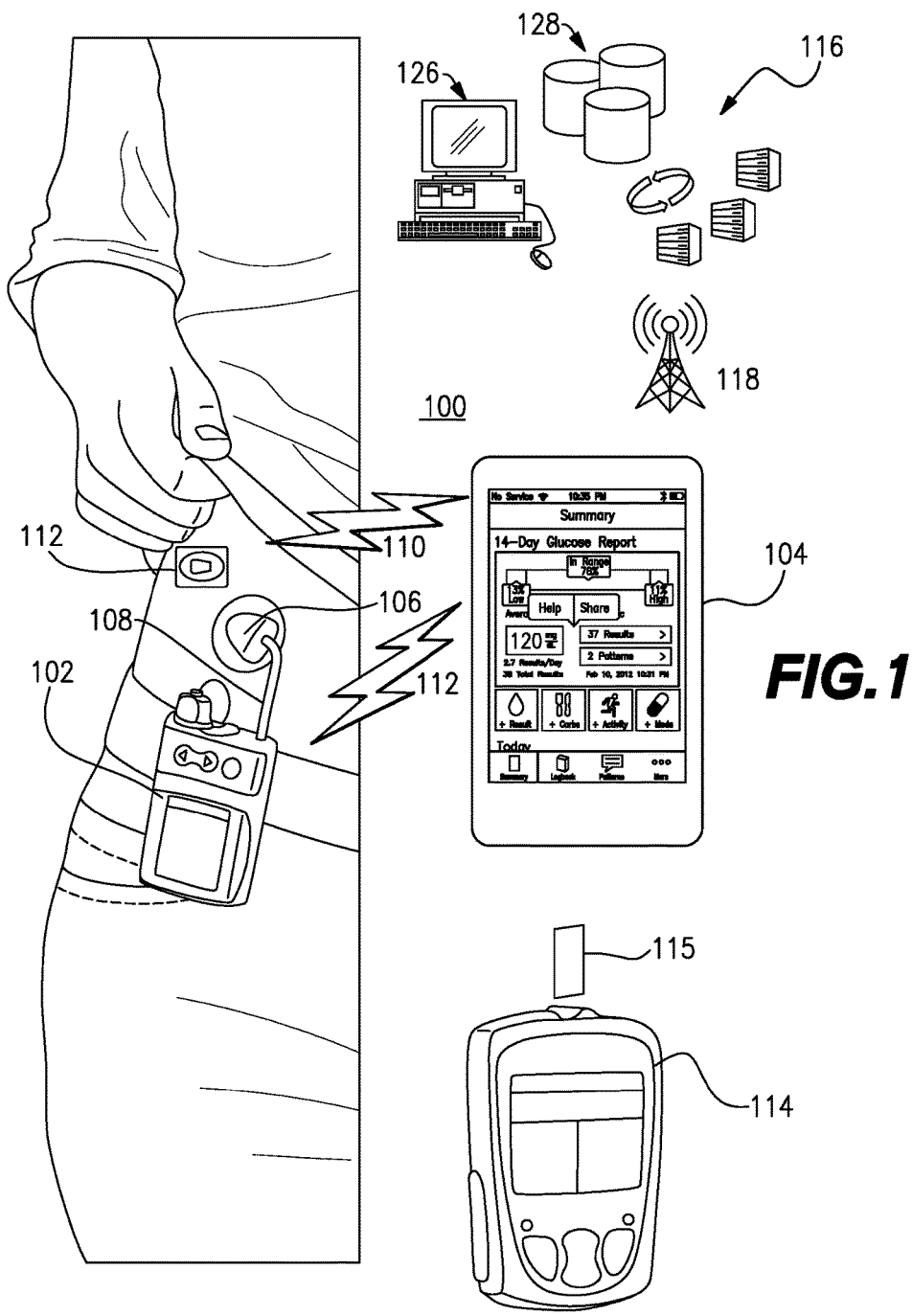
FIG. 1 illustrates the system in which a controller for the pump or glucose monitor(s) is separate from both the infusion pump and the glucose monitor(s) and in which a network can be coupled to the controller to provide near real-time monitoring.

FIG. 1 illustrates a drug delivery system 100 according to an exemplary embodiment that utilizes the principles of the invention. Drug delivery system 100 includes a drug delivery device 102 and a remote controller 104. Drug delivery device 102 is connected to an infusion set 106 via flexible tubing 108.

Figure 6:
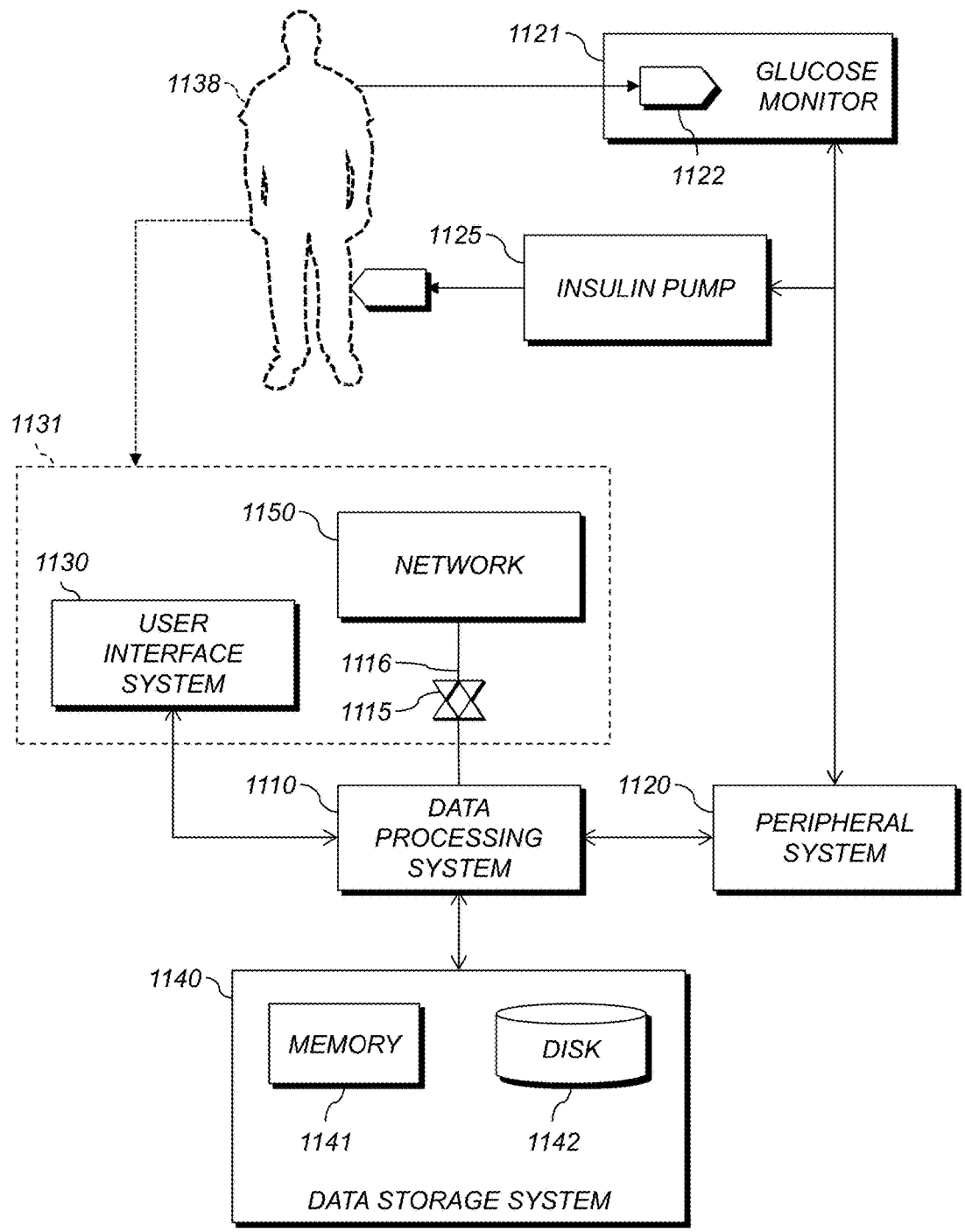
FIG. 6 shows various embodiments of apparatus for the delivery of insulin.

Drug delivery device 102 is configured to transmit and receive data to and from remote controller 104 by, for example, radio frequency communication 112. Drug delivery device 102 may also function as a stand-alone device with its own built in controller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, blood glucose information, basal, bolus, insulin to carbohydrates ratio or insulin sensitivity factor, to name a few. The controller 104 is configured to include an MPC controller 10 that has been programmed to receive continuous glucose readings from a CGM sensor 112. Data transmitted from remote controller 104 to insulin delivery device 102 may include glucose test results and a food database to allow the drug delivery device 102 to calculate the amount of insulin to be delivered by drug delivery device 102. Alternatively, the remote controller 104 may perform basal dosing or bolus calculation and send the results of such calculations to the drug delivery device. In an alternative embodiment, an episodic blood glucose meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities. Examples of micro-controllers that can be used are discussed below with reference to data processing system 1110 (FIG. 6).

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, a server 128 to a memory storage, a personal digital assistant, a mobile telephone, a hospital base monitoring station or a dedicated remote clinical monitoring station.

Drug delivery device 102 includes electronic signal processing components including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected to an infusion set 108/106 and into the body of the user.

Glucose levels or concentrations in physiological fluid (e.g., blood, saliva, or interstitial fluid) of a subject can be determined by the use of the CGM sensor 112. The CGM sensor 112 utilizes amperometric electrochemical sensor technology to measure glucose with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the subject's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous glucose sensor from the Dexcom Seven System® (manufactured by DEXCOM Inc.) can also be utilized with the exemplary embodiments described herein.

In one embodiment of the invention, the following components can be utilized as a system for management of diabetes that is akin to an artificial pancreas: OneTouch Ping® Glucose Management System by Animas Corporation that includes at least an infusion pump and an episodic glucose sensor; and DexCom® SEVEN PLUS® CGM by DexCom Corporation with interface to connect these components and programmed in the MATLAB® language and accessory hardware to connect the components together; and control algorithms in the form of an MPC that regulates the rate of insulin delivery based on the glucose level of the patient, historical glucose measurement and anticipated future glucose trends, and patient specific information.

Figure 2:
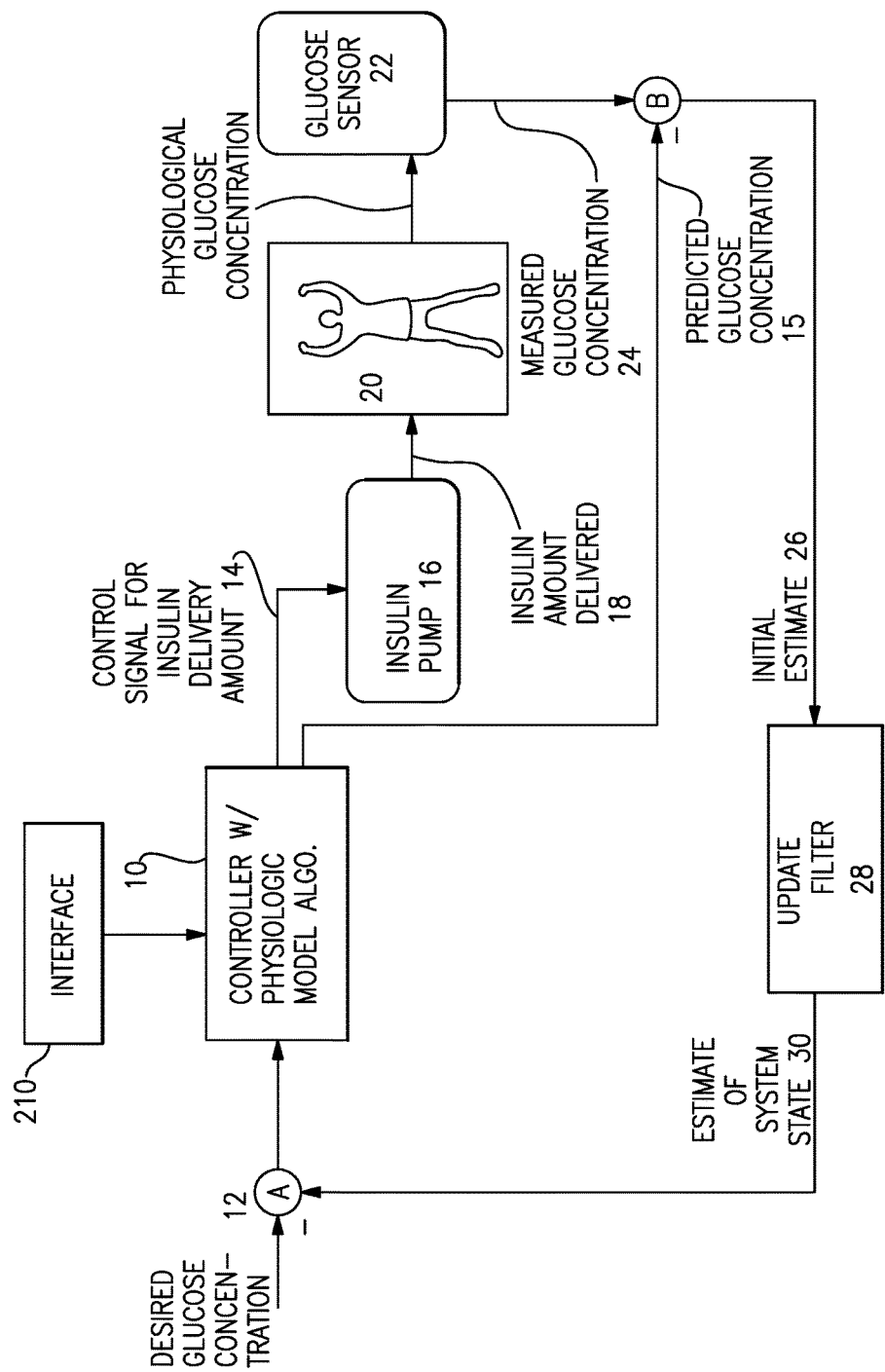
FIG. 2 is a schematic of a control system for managing blood glucose using an insulin pump.

FIG. 2 is a schematic of a control system according to various embodiments for managing blood glucose using an insulin pump. In particular, FIG. 2 provides for an MPC programmed into a control logic module 10 that is utilized in controller 104 (FIG. 1). MPC logic module 10 receives a desired glucose concentration or range of glucose concentration 12 (along with any modification from an update filter 28 so that it is able to maintain the output (i.e., glucose level) of the subject within the desired range of glucose levels.

Referring to FIG. 2, the first output 14 of the MPC-enabled control logic 10 can be a control signal to an insulin pump 16 to deliver a desired quantity of insulin 18 into a subject 20 at predetermined time intervals, which can be indexed, e.g., every 5 minutes using time interval index k. A second output in the form of a predicted glucose value 15 can be utilized in control junction B. A glucose sensor 22 (or 112 in FIG. 1) measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the control logic 10 to further refine the control signal 14 to the pump 16 (or 102 in FIG. 1). A tuning factor can be used with the MPC controller 10 to "tune" the controller in its delivery of the insulin, as discussed below. In various aspects, signals from interface 210 are used by MPC controller 10, as will be discussed. Interface 210 can include one or more touch-screens, buttons, network connections, keyboards, pointing devices, or other devices for receiving data or instructions from humans (e.g., subjects or medical professionals) or other computer systems.

The MPC logic used in controller 10 controls a subject glucose level to a safe glucose zone, with the lower blood glucose limit of the zone varying between 80-100 mg/dL and the upper blood glucose limit varying between about 140-180 mg/dL; the algorithm will henceforth be referred to as the "zone MPC". Controlling to a target zone is, in general, applied to controlled systems that lack a specific set point with the controller's goal being to keep the controlled variable, (CV), for example the glucose values, in a predefined zone. Control to zone (i.e., a euglycemic zone) is highly suitable for the artificial pancreas because of the absence of a natural glycemic set point. Moreover, an inherent benefit of control to zone is the ability to limit pump actuation/activity in a way that if glucose levels are within the zone then no extra correction shall be suggested.

In real-time, the insulin delivery rate $I_D$ from the zone MPC law is calculated by an on-line mathematical optimization (e.g., an operation to find minima or maxima of a function), which evaluates at each sampling time the next insulin delivery rate. The optimization at each sampling time is based on the estimated metabolic state (plasma glucose, subcutaneous insulin) obtained from the dynamic model stored in module 10.

The MPC of control logic 10 incorporates an explicit model of human T1DM glucose-insulin dynamics. The model is used to predict future glucose values and to calculate future controller moves that will bring the glucose profile to the desired range. MPC in controllers can be formulated for both discrete- and continuous-time systems; the controller is set in discrete time, with the discrete time (stage) index k referring to the epoch of the $k^{th}$ sample occurring at continuous time $t=K \cdot T_s$, where $T_s=5$ min is the sampling period. Software constraints ensure that insulin delivery rates are constrained between minimum (i.e., zero) and maximum values. The first insulin infusion (out of N steps) is then implemented. At the next time step, k+1, based on the new measured glucose value and the last insulin rate, the process is repeated.

Specifically, we start with the original linear difference model used for zone MPC:

$$G'(k)=a_1 G'(k-1)+a_2 G'(k-2)+a_3 G'(k-3)+a_4 G'(k-4)+a_5 G'(k-5)+bI_M(k-4)$$

$$I_M(k)=c_1 I_M(k-1)+c_2 I_M(k-2)+d_1 I'_D(k-1)+d_2 I'_D(k-2) \quad \text{Eq. (1)}$$

where:
k is the discrete time interval index having a series of indexing counters where k=1, 2, 3 . . . .
G' is the measured glucose concentration
$I_M$ is the "mapped insulin" which is not a measured quantity
$I'_D$ is the delivered insulin or a manipulated variable
and coefficients $a_1 \sim 2.993$; $a_2 \sim (-3.775)$; $a_3 \sim 2.568$; $a_4 \sim (-0.886)$; $a_5 \sim 0.09776$; $b \sim (-1.5)$; $c_1 \sim 1.665$; $c_2 \sim (-0.693)$; $d_1 \sim 0.01476$; $d_2 \sim 0.01306$.

Using an FDA-accepted metabolic simulator, as known to those skilled in the art, Eq. (1) can be reduced to the following linear difference model in Equation (2):

$$\begin{aligned}
\text{(a) } G'(k) =\; & 2.993 G'(k-1) - 3.775 G'(k-2) + \\
& 2.568 G'(k-3) - 0.886 G'(k-4) + 0.09776 G'(k-5) - \\
& 1.5 I_M(k-4) + 0.1401 Meal_M(k-2) + 1.933 Meal_M(k-3) \\
\text{(b) } I_M(k) =\; & 1.665 I_M(k-1) - 0.693 I_M(k-2) + \\
& 0.01476 I'_D(k-1) + 0.01306 I'_D(k-2) \\
\text{(c) } Meal_M(k) =\; & 1.501 Meal_M(k-1) + 0.5427 Meal_M(k-2) + \\
& 0.02279 Meal(k-1) + 0.01859 Meal(k-2)
\end{aligned} \quad (2)$$

where:
G' is the glucose concentration output (G) deviation variable (mg/dL), i.e., G'=G−110 mg/dL,
$I_D$' is the insulin infusion rate input ($I_D$) deviation variable (U/h), i.e., $I_D$'=$I_D$−basal U/h,
Meal is the CHO ingestion input (gram-CHO),
$I_M$ is the mapped subcutaneous insulin infusion rates (U/h), and
$Meal_M$ is the mapped CHO ingestion input (gram-CHO).

The dynamic model in Eq. (2) relates the effects of insulin infusion rate ($I_D$), and CHO ingestion input (Meal) on plasma glucose. The model represents a single average model for the total population of subjects. The model and its parameters are fixed.

The second-order input transfer functions described by parts (b) and (c) in Eq. (2) are used to generate an artificial input memory in the zone MPC schema to prevent insulin over-dosing, and consequently prevent hypoglycemia. In order to avoid over-delivery of insulin, the evaluation of any sequential insulin delivery must take into consideration the past administered insulin against the length of the insulin action. However, a one-state linear difference model with a relatively low order uses the output (glycemia) as the main source of past administered input (insulin) "memory." In the face of the model mismatch, noise, or change in the subject's insulin sensitivity, this may result in under- or over-delivery of insulin. This is mitigated by adding two additional states ($I_M$ and $Meal_M$) for the mapped insulin and meal inputs that carry a longer insulin memory.

Zone MPC is applied when the specific set point value of a controlled variable (CV) is of low relevance compared to a zone that is defined by upper and lower boundaries. Moreover, in the presence of noise and model mismatch there is no practical value using a fixed set point. Other details of the derivation for the Zone MPC technique are shown and described in Benyamin Grosman, Ph.D., Eyal Dassau, Ph.D., Howard C. Zisser, M.D., Lois Jovanovič, M.D., and Francis J. Doyle III, Ph.D. *"Zone Model Predictive Control: A Strategy to Minimize Hyper and Hypoglycemic Events"* Journal of Diabetes Science and Technology, Vol. 4, Issue 4, July 2010, and US Patent Application Publication No. 2011/0208156 to Doyle et al., entitled *"Systems, Devices, and Methods to Deliver Biological Factors or Drugs to a Subject,"* with the publication date of Aug. 25, 2011, all which are incorporated by reference as if set forth herein with a copy in the Appendix. Additional details of the Zone MPC are shown and described in US Patent Application Publication No. 20110208156, which is incorporated by reference as if set forth herein with a copy in the Appendix. A related derivation of zone MPC was presented in Maciejowski J M., "PREDICTIVE CONTROL WITH CONSTRAINTS" Harlow, UK: Prentice-Hall, Pearson Education Limited, 2002.

Zone MPC typically divides the range of the controlled variable into three different zones. The permitted range is the control target and it is defined by upper and lower bounds. The upper zone represents undesirable high predicted glycemic values. The lower zone represents undesirable low predicted glycemic values that represent hypoglycemic zone or a pre-hypoglycemic protective area that is a low alarm zone. The zone MPC optimizes the predicted glycemia by manipulating the near-future insulin control moves to stay in the permitted zone under specified constraints. The predicted residuals are defined as the difference between the CV that is out of the desired zone and the nearest bound.

In various aspects, zone MPC is implemented by defining fixed upper and lower bounds as soft constraints. A mathematical optimization process uses weights that switch between zero and some final values when the predicted CVs are in or out of the desired zone, respectively.

Model predictive control operates by mathematically minimizing a cost function. For example, future glucose levels are predicted from past glucose levels and insulin amounts and from the candidate insulin amounts to be delivered in the future, e.g., using linear difference models of insulin-glucose dynamics. A cost is assigned to these predicted glucose levels. For zone MPC, the cost function defines the zone of control by setting cost much lower (e.g., 0) within the zone than out of the zone. Therefore, the cost of future glucose levels causes the optimization to select future $I'_D$ values that will tend to keep the predicted outputs within the zone of control (e.g., a zone defined by upper and lower bounds), rather than future values that will move the predicted outputs towards a specific set point. Optimizing using such a cost function can reduce hypo- and hyperglycemic excursions from the zone of control. The aggressiveness of the controller in reducing excursions is influenced by the cost function, e.g., weights contained therein.

The zone MPC cost function J according to various aspects is:

$$J(I'_D) = Q \cdot \sum_{j=1}^{P} \|G^{zone}(k+j)\| + R \cdot \sum_{j=0}^{M-1} \|I'_D(k+j)\| \text{ s.t.} \quad (3)$$

$$G(k+j) = f[G(k+j-1), I'_D(k+j-1)]$$

$$\forall j = 1, P$$

$$-basal(k+j) \le I'_D(k+j) \le 72$$

$$\forall j = 0, M-1$$

In various embodiments, $I_D'$ is expanded:

$$J(I_D') = \Sigma \|G^{zone}(k+j)\| + R \cdot \Sigma \|I_D(k+j) - basal(k+j)\| \quad (4)$$

where
Q is a weighting factor on the predicted glucose term;
R is a tuning factor on the future proposed inputs in the cost function;
$f$ is the prediction function (in Eq. (2));
vector $I_D$ contains the set of proposed near-future insulin infusion amounts. It is the "manipulated variable" because it is manipulated in order to find the minimum in J; and
basal(t) is the basal delivery rate at time interval t; and
$G^{zone}$ is a variable quantifying the deviation of future model-predicted CGM values G outside a specified glycemic zone. In various embodiments, $G^{zone}$ is:

$$G^{zone} = \begin{cases} 0 & \text{if } G_{ZL} \le G \le G_{ZH} \\ G - G_{ZH} & \text{if } G > G_{ZH} \\ G_{ZL} - G & \text{if } G < G_{ZL} \end{cases} \quad (5)$$

where the glycemic zone is defined by the upper limit $G_{ZH}$ and the lower limit $G_{ZL}$.

Thus, if all the predicted glucose values are within the zone, then every element of $G^{zone}$ is equal to 0, and consequently J is minimized with $I_D$=basal for that time of day, i.e., the algorithm "defaults" to the patient's current basal insulin infusion rate. On the other hand, if any of the predicted glucose values are outside the zone, then $G^{zone} > 0$ and thus contributes to the cost function. In this case, the near-future proposed insulin infusion amounts $I_D$ will deviate from the basal in order to prevent out-of-zone deviation in $G^{zone}$ from ever happening, which will also "contribute" to the cost function. Then, a quantitative balance is found in the optimization, based on the weighting factor R.

In order to solve optimization problem of Equations (2)-(5), a commercially available software (e.g., MATLAB's "fmincon.m" function) can be used. For this function, the following parameters are used for each optimization:

Initial guess for the insulin delivery rates, $I_D(0)$, is the null vector $\vec{0} \in R^M$, e.g., if M=5 the initial guess for each optimization is $$I_D' = [0\ 0\ 0\ 0\ 0].$$

This implies that the initial guess is equivalent to the basal rate.

Maximum number of function evaluations allowed is Max_f=100*M, where M is control horizon as described earlier.

Maximum number of iterations is Max_i=400, which is fixed.

Termination on the cost function values Term_cost=1e−6, which is fixed.

Termination tolerance Term_tol on the manipulated variables $I_D'$ is 1e−6.

The following hard constraints are implemented on the manipulated variables $I_D'(t)$:

$$-basal(t) \le I_D'(t) \le 72 \text{ U/h} \quad (6)$$

where basal is the subject's basal rate as set by the subject or his/her physician, expected in the range 0.6-1.8 U/hr.

Although the values of control horizon parameter M and prediction horizon parameter P have significant effects on the controller performance, and are normally used to tune an MPC based controller, they can be heuristically tuned based on knowledge of the system. Tuning rules are known to those skilled in the field. According to these rules M and P may vary between:

$$2 \le M \le 10$$

$$20 \le P \le 120 \quad (7)$$

In various embodiments, M=5 and P=108.

The ratio of the output error weighting factor Q and the input change weighting matrix or tuning factor R may vary between:

$$10 \le \frac{R}{Q} \le 1000 \quad (8)$$

In various embodiments, R/Q=500.

Once the controller is initialized and switched on, real-time calculations take place every five minutes, corresponding to the sample time for the glucose sensor. The first element of $I_D$ is delivered as an insulin dose to the patient through the insulin pump, five minutes elapse, a new CGM reading becomes available, and the process repeats. In various aspects, the controller delivers the basal rate until M samples have been taken; this is sometimes referred to as a "burn-in" period. It is noted that the future control moves are hard-constrained, set by the insulin pump's ability to deliver a maximum rate of insulin and the inability to deliver negative insulin values. Other details of related subject matter including state estimator, and other MPC are provided by Rachel Gillis et al., "*Glucose Estimation and Prediction through Meal Responses Using Ambulatory Sub-* ject Data for Advisory Mode Model Predictive Control" Journal of Diabetes Science and Technology Vol. 1, Issue 6, November 2007 and by Youqing Wang et al., "*Closed-Loop Control of Artificial Pancreatic β-Cell in Type* 1 *Diabetes Mellitus Using Model Predictive Iterative Learning Control*" IEEE Transactions on Biomedical Engineering, Vol. 57, No. 2, February 2010, which are hereby incorporated by reference into this application as if fully set forth herein.

It is known that the tuning parameter (designated here as "R") can have a significant effect on the quality of the glucose control. The parameter—known as the aggressiveness factor, gain, and other names—determines the speed of response of the algorithm to changes in glucose concentration. A relatively conservative value of R results in a controller that is slow to adjust insulin infusion amounts (relative to basal) in response to changes in glucose; on the other hand, a relatively aggressive value of R results in a controller that is quick to respond to changes in glucose. In principle, an aggressive controller would result in the best glucose control if 1) the available glucose measurements are accurate, and moreover 2) the model predictions of future glucose trends are accurate. If these conditions are not true, then it may be safer to use a conservative controller.

In various aspects, basal rate basal(t) changes over time. For example, the basal rate can be lower at night (e.g., 0.5 U/h), when metabolism is low, and higher during the day. The cost function J above includes an $I_D$-basal term, so there is a cost to deviating from basal. The Zone MPC controller is driven to keep $I_D$ close to basal unless doing so raises the $G^{zone}$ term in J more than a deviation from basal would.

The mathematical theory of imaginary numbers provides that any number of square roots of −1 can be defined. For conventional complex numbers $z=a+bi_1$, $i_1=\sqrt{-1}$, a is the "real part" of z (Re(z)), and b is the "imaginary part" of z (Im(z)). The complex numbers can be extended by defining a second square root of −1, $i_2$, such that $i_1 i_2 = i_2 i_1$. A bicomplex number w is then $$w = z_1 + i_2 z_2$$

for complex numbers $z_1$, $z_2$, or $$w = x_0 + i_1 x_1 + i_2 x_2 + i_1 i_2 x_3$$

for real numbers $x_1 \ldots x_4$. Throughout this disclosure, italics are not significant in reference to bicomplex or quaternion (discussed below) components. In this disclosure, $x_0$ is referred to as the "real part" of w, $x_1$ is the "first imaginary part," x2 is the "second imaginary part," and $x_3$ is the "combined imaginary part." The resulting number system is isomorphic ($\Leftrightarrow$) to 2×2 matrices:

$$i_1 \leftrightarrow \begin{pmatrix} i & 0 \\ 0 & i \end{pmatrix} \quad i_2 \leftrightarrow \begin{pmatrix} 0 & i \\ i & 0 \end{pmatrix}$$

for some $i = \sqrt{-1}$. The multiplicative identity in this system is isomorphic to $$1 \leftrightarrow \begin{pmatrix} 1 & 0 \\ 0 & 1 \end{pmatrix}$$

and the product of $i_1$ and $i_2$, which commute under multiplication, is $$i_1 i_2 \leftrightarrow \begin{pmatrix} 0 & -1 \\ -1 & 0 \end{pmatrix}$$

Equality-testing or addition of two bicomplex numbers, scalar multiplication of a real by a bicomplex number, and computing the norm of a bicomplex number are defined as if the bicomplex numbers were four-component vectors ($x_0$, $x_1$, $x_2$, $x_3$). Multiplication of two bicomplex numbers is performed as if they were polynomials in $i_1$ and $i_2$, and is commutative. Specifically, $$(x_0+x_1i_1+x_2i_2+x_3i_1i_2) \times (y_0+y_1i_1+y_2i_2+y_3i_1i_2) = (x_0y_0 - x_1y_1 - x_2y_2 + x_3y_3) + i_1(x_0y_1+x_1y_0-x_2y_3-x_3y_2) + i_2(x_0y_2-x_1y_3+x_2y_0-x_3y_1) + i_1i_2(x_0y_3+x_1y_2+x_2y_1+x_3y_0)$$

(see Price, G. Baley. *An Introduction to Multicomplex Spaces and Functions*. New York: Marcel Dekker, Inc., 1991. ISBN 0-8247-8345-X. Page 7, eq. 2.)

An alternative extension to the complex numbers is the quaternion system $\mathbb{H}$. In this system, three unique square roots of −1 are defined, $i_Q$, $j_Q$, and $k_Q$. The subscript "Q" is used to differentiate the quaternion bases (conventionally denoted "i," "j," and "k") from indices i, j in matrices and vectors, and time interval indices k used throughout with reference to MPC. The quaternion bases are related as:

$$i_Q^2 = j_Q^2 = k_Q^2 = i_Q j_Q k_Q = -1.$$

A quaternion q is then $$q = x_0 + x_1 i_Q + x_2 j_Q + x_3 k_Q.$$

Quaternion addition, scalar multiplication, and Euclidean norm are performed as if the $x_n$ were a four-element vector in $[x_0 \ x_1 \ x_2 \ x_3] \in \mathbb{R}^4$. Quaternions are isomorphic to:

$$1 \leftrightarrow \begin{pmatrix} 1 & 0 \\ 0 & 1 \end{pmatrix} \quad i_Q \leftrightarrow \begin{pmatrix} i & 0 \\ 0 & -i \end{pmatrix}$$

$$j_Q \leftrightarrow \begin{pmatrix} 0 & 1 \\ -1 & 0 \end{pmatrix} \quad k_Q \leftrightarrow \begin{pmatrix} 0 & i \\ i & 0 \end{pmatrix}$$

Multiplication of two quaternions is performed as if they were polynomials in i, j, k, and is not commutative. For $p = p_0 + p_1 i_Q + p_2 j_Q + p_3 k_Q$ and $q = q_0 + q_1 i_Q + q_2 j_Q + q_3 k_Q$, all $p_n$, $q_n \in \mathbb{R}$, $$p \times q = (p_0 q_0 - p_1 q_1 - p_2 q_2 - p_3 q_3) + (p_0 q_1 + p_1 q_0 + p_2 q_3 - p_3 q_2) i_Q + (p_0 q_2 - p_1 q_3 + p_2 q_0 + p_3 q_1) j_Q + (p_0 q_3 + p_1 q_2 - p_2 q_1 + p_3 q_0) k_Q$$

In this disclosure, the term "multicomplex number" refers to a bicomplex number or a quaternion. A multicomplex number as defined herein has first, second, and third imaginary components. For bicomplex numbers, these are the $i_1$, $i_2$, $i_1 i_2$ components, respectively. For quaternions, they are the $i_Q$, $j_Q$, $k_Q$ components, respectively.

In optimization problems, a "quadratic form" approximation of the function near a particular point can be used. For example, given function $f(x)$, $$f(x+s_k) \approx f(x) + \phi(s_k),$$

the subscript k referring to iteration k of an optimization loop, where $$\phi(s_k) = \tfrac{1}{2} s_k^T M_k s_k + s_k^T g_k,$$

$g_k$ is the Jacobian of $f$ at x, and $M_k$ is the Hessian of $f$ at x. $\phi(s_k)$ is the second term of the Taylor expansion of $f$ at x. It is also known that a minimum of $\phi(s_k)$ is at the solution of $M_k s_k = -g_k$, $M_k$ and $s_k$ possibly having been pre-conditioned or scaled before solving the system of equations. The point at which $\phi(s_k)$ is minimized is the point at which $f(x+s_k)$ is minimized by the definition above of $\phi(s_k)$, to the extent to which the Taylor approximation is valid. Therefore, an optimization routine can proceed from x to $x+s_1$ to $x+s_1+s_2$ . . . as it searches for a minimum of $f$.

In The Jacobian g of a multivariate function is a vector or matrix that includes the partial derivatives of that function with respect to each of the variables. The Jacobian "at a point" is that vector or matrix, evaluated at a point of interest. It is not always possible to symbolically determine the partial derivatives of a function of interest, e.g., a cost function J as defined herein. Therefore, there is a need for a way of computing the Jacobian of a function $f$ (e.g., cost function J) at a point x by evaluating only the function and not its derivatives. As discussed above, the conventional approach involves computing $$\frac{\partial f}{\partial x_i} = \lim_{\varepsilon \to 0} \frac{f(x+\varepsilon) - f(x)}{\varepsilon}$$

but this is subject to round-off error that prevents $\epsilon$ from being as small as desired for accuracy. According to various inventive aspects described herein, the Jacobian is computed in a complex number space. This avoids the subtraction in the numerator of the conventional approach above, significantly reducing the severity of round-off error. Correspondingly, Hessians can be computed in a bicomplex space. Together, these computations permit using a quadratic form to mathematically optimize (minimize or maximize) a function.

FIGS. 3A-3E are a flowchart illustrating exemplary methods for determining a local extremum (minimum or maximum) of a function on an n-dimensional space. Through this description, "extremum" refers to whichever is being sought, whether a minimum or a maximum. The steps of the flowchart can be performed automatically using a controller. Processing begins with step 310.

This description is in terms of a function $f$ evaluated at n-dimensional point(s) x. An example of $f$ is the cost function J described above (Eq. 3), and an example of x is the initial guess $I'_D(0)$ described above. Point x, e.g., $I'_D(0)$, is an n×1 vector whose elements are numbered 1 . . . n. The function $f$ is defined to return values in $\mathbb{R}$ (not $\mathbb{C}$ or any $\mathbb{C}_k$, k>0) for inputs in $\mathbb{R}^k$, $\forall k \geq 0$. In various embodiments, step 310 selects a starting point x, step 320 computes the Jacobian of $f$ at x, and step 330 computes the Hessian of $f$ at x. Step 340 uses the Jacobian and Hessian to find a delta $\Delta x$ towards a local extremum, and step 350 determines the endpoint of that step $x+\Delta x$. Decision step 360 determines whether the computation has converged to an extremum of $f$. If not, process can repeated from x ("DO NOT UPDATE") or from the point at the end of the step $x+\Delta x$ ("UPDATE"; step 370). Examples of updating or not are discussed below. In at least one embodiment, decision step 360 includes determining whether a number of iterations has exceeded a threshold, whether $|f(x)-f(x+s)|$ is less than a threshold, or whether s is less than a threshold, and, if so, terminating, either reporting failure or reporting success with x or x+s as the result.

Specifically, in step 310, a value for a real-type test point x in the n-dimensional space is selected. "Real-type" signifies that $x=[x_1 \ldots x_n]$, $\forall i \in [1,n]$: $x_i \in \mathbb{R}$. The selection can be done by choosing pseudorandom coordinate(s), by receiving the test point (e.g., via an interface to a user or other controller), by assigning a fixed starting point (e.g., $\vec{0}$), or by determining a test point based on characteristics of $f$.

"Type" as used herein refers to the category of numbers to which the elements of a point belong. For example, since test point x is real-type, $x \in \mathbb{R}^n$, and $f: \mathbb{R}^n \to \mathbb{R}$ (in this example; $f$ can also have multiple outputs). Here, $\mathbb{R}$ is also denoted $\mathbb{C}_0$. Step 310 is followed by step 320.

Figure 3A:
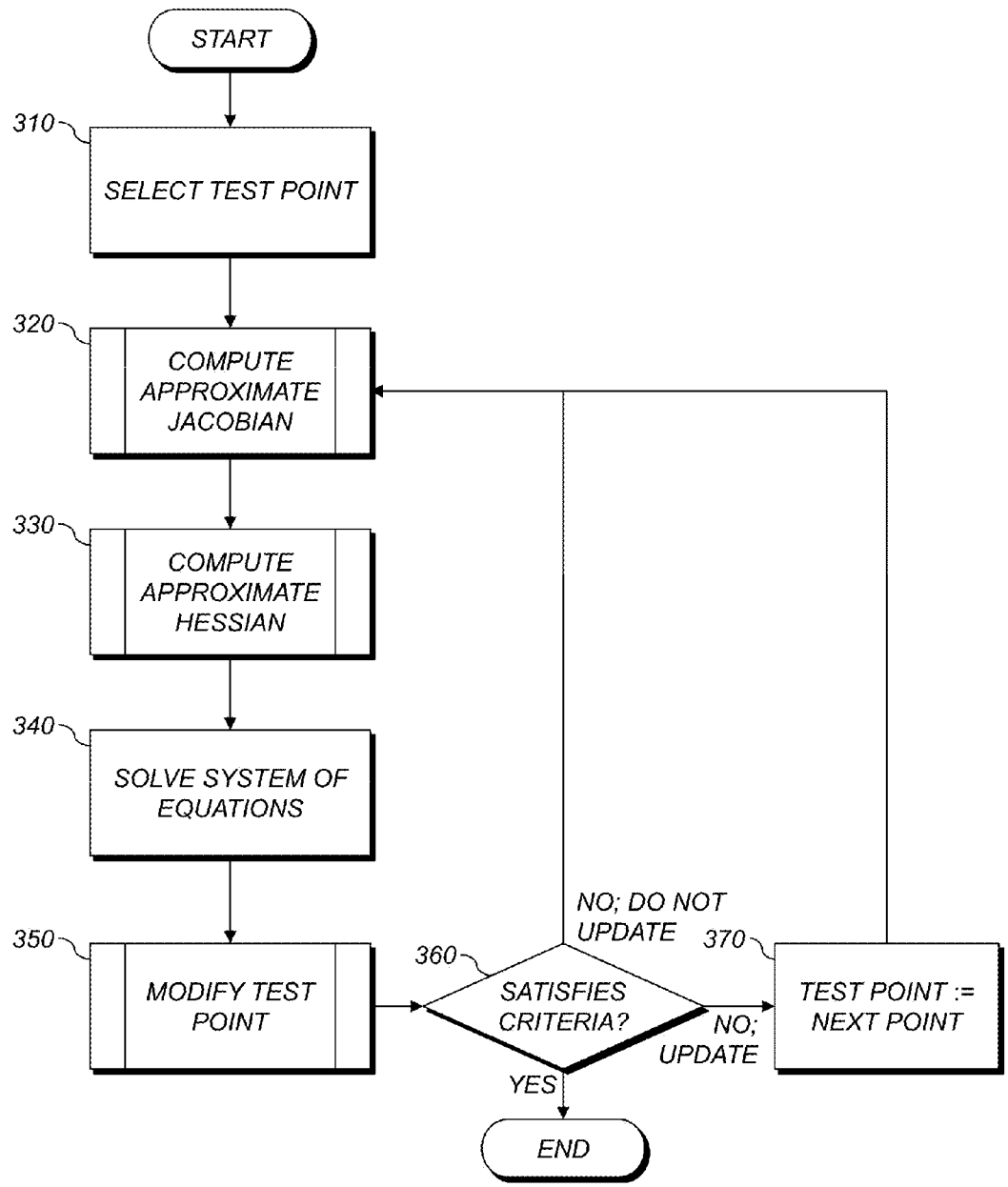
FIGS. 3A-3E are a flowchart illustrating exemplary methods for determining an extremum of a function.
Figure 3B:
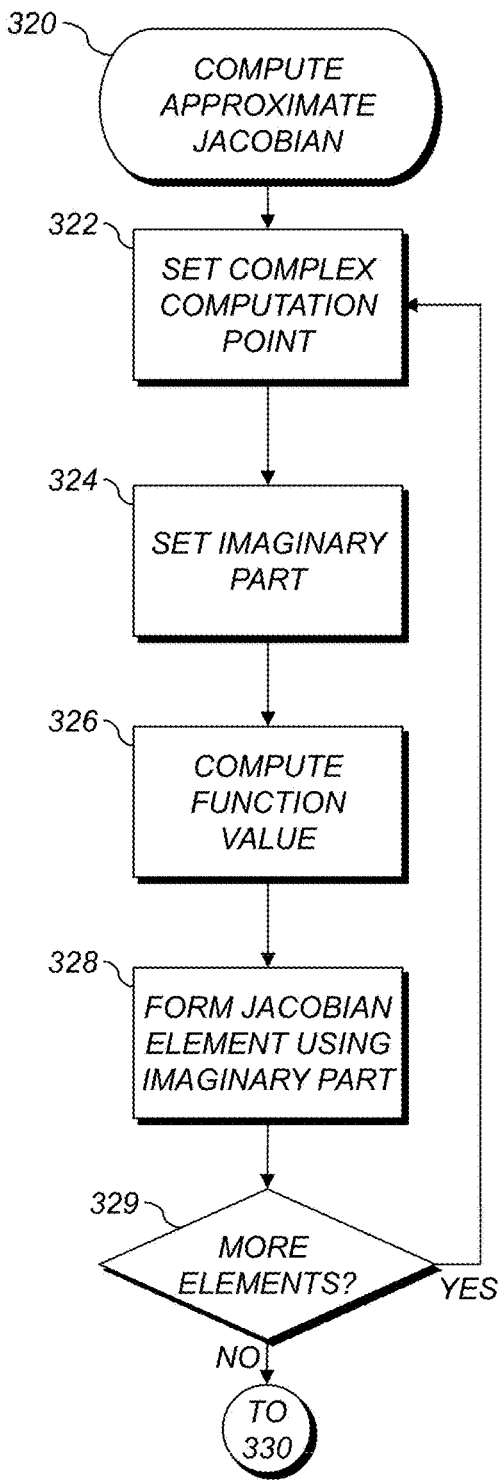

In step 320, an approximate Jacobian G of the function $f$ at the test point x is computed. Referring to FIG. 3B, step 320 includes steps 322, 324, 326, and 328, and decision step 329. Decision step 329 causes steps 322-328 to be repeated for each dimension i of the n dimensions. The order in which the dimensions are visited is irrelevant.

In step 322, the computation is moved from $\mathbb{C}_0$ to $\mathbb{C}_1$, the complex numbers. Specifically, a complex-type computation point $c \in \mathbb{C}_1^n$ is set equal to the test point x: $c_i := x_i + 0i$, $\forall i \in 1 \ldots n$. That is, computation point c can hold complex values, but does not at first.

In step 324, an imaginary part of element i of c is set equal to a nonzero increment $\delta \in \mathbb{R}$. The increment can be negative or positive. Specifically, $c_i := c_i + \delta i$. Step 324 can be carried out during a loop over all elements in step 322. Note that the "imaginary part" Im(z) of a complex number $z=a+bi$ is b, not bi, by definition. After this step, e.g., for n=5, i=2, $$c = \begin{bmatrix} x_1 \\ x_2 + \delta i \\ x_3 \\ x_4 \\ x_5 \end{bmatrix}.$$

In step 326, a complex-type value $f(c)$ of the function $f$ at c is computed. These values can be computed using conventional complex-number operations of e.g., multiplication and addition. For example, this could be a computation of $J([0 \ \delta i \ 0 \ 0 \ 0]^T) \to \mathbb{C}$. The result is a scalar (a single number, here of complex type). This is the value of the function at the n-dimensional test point x, with x permuted in one of its dimensions by $\delta i$.

In step 328, the imaginary part of the complex-type scalar computed function value is divided by the increment to form element i of the Jacobian. Continuing the example above, and letting $g:n \times 1 = [g_1 \ g_2 \ \ldots \ g_n]^T$, $$g_2 = \frac{\text{Im}\left(f\left(\begin{bmatrix} x_1 \\ x_2 + \delta i \\ x_3 \\ x_4 \\ x_5 \end{bmatrix}\right)\right)}{\delta} \in \mathbb{R}.$$

This is a reasonable computation because, by construction, $b \in \mathbb{R}^n$. Therefore, $f(b) \in \mathbb{R}$ by the definition above. Thus $\text{Im}(f(b))=0$. The above equation for $g_2$ is thus the finite-difference approximation, but the subtraction is a subtraction of zero and therefore does not need to be performed:

$$g_2 = \frac{\text{Im}\left(f\left(\begin{bmatrix} x_1 \\ x_2 + \delta i \\ x_3 \\ x_4 \\ x_5 \end{bmatrix}\right)\right) - \text{Im}\left(f\left(\begin{bmatrix} x_1 \\ x_2 \\ x_3 \\ x_4 \\ x_5 \end{bmatrix}\right)\right)}{\delta} \in \mathbb{R}.$$

$$= \frac{\text{Im}\left(f\left(\begin{bmatrix} x_1 \\ x_2 + \delta i \\ x_3 \\ x_4 \\ x_5 \end{bmatrix}\right)\right) - 0}{\delta}$$

$$= \frac{\text{Im}\left(f\left(\begin{bmatrix} x_1 \\ x_2 + \delta i \\ x_3 \\ x_4 \\ x_5 \end{bmatrix}\right)\right)}{\delta}$$

As a result, the subtraction step is no longer required. The perturbation $\delta$ is extracted from the imaginary component only, removing the need to subtract two numbers very close to one another. Truncation error remains, but $\delta$ can now be made much smaller than with prior schemes without incurring significant round-off error. Various processors can implement the above computation using a single multiply of $1/\delta$, which is quite efficient. In various examples, function $f$ is defined such that $\text{Re}(f(b)) = \text{Im}(f(a+bi))$, but this structure is not required.

In decision step 329, the controller determines whether all n dimensions have been processed. If so, the next step is step 330. If not, the next step is step 322 for another dimension. In this way, $f$ is evaluated at, e.g., $$\begin{bmatrix} x_1 + \delta i \\ x_2 \\ x_3 \\ x_4 \\ x_5 \end{bmatrix}, \begin{bmatrix} x_1 \\ x_2 + \delta i \\ x_3 \\ x_4 \\ x_5 \end{bmatrix}, \begin{bmatrix} x_1 \\ x_2 \\ x_3 + \delta i \\ x_4 \\ x_5 \end{bmatrix}, \begin{bmatrix} x_1 \\ x_2 \\ x_3 \\ x_4 + \delta i \\ x_5 \end{bmatrix}, \begin{bmatrix} x_1 \\ x_2 \\ x_3 \\ x_4 \\ x_5 + \delta i \end{bmatrix},$$

and each one of those evaluations results in one element of the Jacobian g ($g_1 \ldots g_5$, respectively) being filled in. These computations can be performed in series or parallel, in any combination, as can the Hessian computations described below. Moreover, the Jacobian and Hessian can be computed in either order, or simultaneously.

Referring back to FIG. 3A, in step 330, an approximate Hessian H of the function $f$ is computed at the test point x. Referring to FIG. 3B, step 330 includes steps 331, 332, 333, 334, 335, and decision step 326. Decision step 326 causes steps 331-335 to be repeated for each pair of dimensions (i,j), each i and j one of the n dimensions. For example, for n=2, the loop is repeated four times. These computations can also be performed in parallel or in a combination of series and parallel.

In step 331, the computation is moved from $\mathbb{C}_0$ to a multicomplex number space. The following discussion relates to $\mathbb{C}_2$, the bicomplex numbers; quaternions are discussed below. As used herein, the multicomplex type can be a bicomplex type and the third imaginary part can be a combined imaginary part, as described below. The multicomplex type can alternatively be a quaternion type, and the first, second, and third imaginary parts can be $i_Q$, $j_Q$, and $k_Q$ parts, respectively.

In step 331, a multicomplex-type (here, bicomplex-type) computation point b is set equal to the test point x. As for step 322, above, the three imaginary parts of b are initially zero. Specifically, $$b := \begin{bmatrix} x_1 + 0i_1 + 0i_2 + 0i_1 i_2 \\ \vdots \\ x_n + 0i_1 + 0i_2 + 0i_1 i_2 \end{bmatrix}.$$

In step 332, a first imaginary part of element i of b is set equal to a nonzero first increment $\delta_1 \in \mathbb{R}$, which can be positive or negative. In step 333, a second imaginary part of element j of b is set equal to a nonzero second increment $\delta_2 \in \mathbb{R}$, which can be positive or negative. The result is that, for, e.g., n=5, i=1, j=2, $$b := \begin{bmatrix} x_1 \\ x_2 + \delta_1 i_1 + 0i_2 + 0i_1 i_2 \\ x_3 + 0i_1 + \delta_2 i_2 + 0i_1 i_2 \\ x_4 \\ x_5 \end{bmatrix}.$$

In step 334, a bicomplex-type value $f(b)$ of the function $f$ is computed at b. This can be performed using bicomplex operations such as addition and multiplication, described above. In general, $f(b)$ is a multicomplex-type value computed from a multicomplex-type b.

In step 335, the third imaginary part, which is the combined imaginary part $\text{Im}_{12}(b)$ for bicomplex, of the computed bicomplex-type function value $f(b)$ is divided by the product $\delta_1 \delta_2$ of the first and second increments to form element (i, j) of the Hessian. Continuing the example above, and letting $$H: n \times n = \begin{bmatrix} H_{11} & \cdots & H_{1n} \\ \vdots & \ddots & \vdots \\ H_{n1} & \cdots & H_{nn} \end{bmatrix},$$

$$Im_{12}(x_0 + x_1 i_1 + x_2 i_2 + x_3 i_1 i_2) \stackrel{def}{=} x_3,$$

$$H_{23} = \frac{Im_{12}\left(f\left(\begin{bmatrix} x_1 \\ x_2 + \delta_1 i_1 \\ x_3 + \delta_2 i_2 \\ x_4 \\ x_5 \end{bmatrix}\right)\right)}{\delta_1 \delta_2} \in \mathbb{R}.$$

As for the case of complex numbers discussed above, $f(b) \in \mathbb{R}$ for $b \in \mathbb{R}^n$. The expression above for $H_{23}$ is thus the finite-difference approximation with the subtrahend in the numerator being 0. Therefore, two very close numbers are not subtracted from each other, greatly reducing the severity or occurrence of round-off error.

From decision step 339, the next step is step 332 if there are more (i,j) pairs for which to compute Hessian elements. In this way, all n×n elements of the Hessian are computed. If all elements have been computed, the next step is step 340.

For quaternions, b is initially set to the vector with elements $x_i+0i+0j+0k$, $\forall i \in [1,n]$. The $i_Q$ and $j_Q$ components are permuted as described above for the $i_1$ and $i_2$ components, respectively. The $k_Q$ component (third imaginary part) is extracted to determine the Hessian, as described above for the $i_1 i_2$ component. Specifically, continuing the example above but using quaternions rather than bicomplex numbers as the multicomplex numbers:

$$H: n \times n = \begin{bmatrix} H_{11} & \cdots & H_{1n} \\ \vdots & \ddots & \vdots \\ H_{n1} & \cdots & H_{nn} \end{bmatrix},$$

$$Im_k(x_0 + x_1 i_Q + x_2 j_Q + x_3 k_Q) \stackrel{def}{=} x_3,$$

$$H_{23} = \frac{Im_k\left(f\left(\begin{bmatrix} x_1 \\ x_2 + \delta_1 i_Q \\ x_3 + \delta_2 j_Q \\ x_4 \\ x_5 \end{bmatrix}\right)\right)}{\delta_1 \delta_2} \in \mathbb{R}.$$

Referring back to FIG. 3A, in step 340, a system of equations defined by the approximate Hessian and the approximate Jacobian is solved to find a delta. A "delta" as used herein is a vector which, when placed starting at x, ends at a point such that $f(y)$ may be closer to the desired extremum than $f(x)$. A "delta" is sometimes referred to in the art as a "step." A "delta" is not the same as any increment $\delta$, $\delta_1$, $\delta_2$. An exemplary system is $Hs=-g$ for delta s. The system can be solved by any desired mathematical technique for solving systems of equations or for solving matrix equations. In an example, a preconditioned conjugate gradient algorithm is used to solve the system; at least two iterations can be executed. In an example, the extremum sought is or comprises a minimum, and the system is solved to find a delta s that will reduce the value of function $f$ (e.g., a cost function). Step 340 is followed by step 350.

In step 350, the test point x is modified according to the delta, e.g., by summing, to form a next point y. For example, $y := x + s$. Since x and s are both n-element vectors, y is also an n-element vector, representing a point in n-dimensional space.

In decision step 360 the controller determines whether the next point y satisfies selected convergence criteria. If so, the method is complete and y is the extremum of $f$ or an approximation thereto. If not, the next step is step 370. An example of a convergence criterion is that $|s|<k$ for some threshold k. Another example is that $|f(y)-f(x)|<k$, again for a threshold k. Another example is that $|f(y)-f(x)|<k(1+|f(x)|)$ for some k.

In step 370, the value of the next point is assigned to the test point, e.g., $x := y$. The computing steps and the modifying through the determining step are then repeated. The next step is thus step 320. In this way, x moves closer to the desired extremum by moving in steps, each step according to the quadratic-form estimation of the function in the vicinity of the origin of that step.

In an example of step 360, a trust-region reflective optimization technique is used. Armijo-Goldstein line search can be used with this method to find function minima along a line. In trust-region techniques, the fact that the quadratic approximation is only valid over a limited volume of the n-dimensional space around x is used to guide the optimization process. As optimization proceeds, next point y is constrained to be within the trust region to reduce the incidence or severity of approximation-induced error. The size of the trust region is expanded or contracted at each step to balance reduction in error, which involves smaller trust regions, with rapid convergence, which requires large deltas and thus large trust regions. In these examples, referring to FIG. 3D, modifying step 350 includes step 351 of selecting a value for a trust region. In step 352, the next point y is computed as the sum of the test point x and the delta s (component-by-component). That sum is clipped within the trust region. The clipping can be performed by boundary-intersection or clipping algorithms known in the computer-graphics and computational geometry art. In this example, step 360 includes steps 361, 363, 365, 365, and 366, and decision steps 362 and 364.

In step 361, a value for a trust region is selected (e.g., received, chosen randomly, selected from a table, or other options described above for receiving the test point). This value is a spatial region, however defined. It can be a radius of a (hyper)sphere around x, a series of (hyper)planes or other geometric features that bound the test region, a combination of those, or any other description of a region in n-dimensional space.

In decision step 362, the controller determines whether the next point y is in fact closer to the extremum than test point x, i.e., whether the value of the function $f(y)$ at the next point y is closer to the extremum (i.e., less positive or more negative, for a minimizer) than the value of the function $f(x)$ at the test point x. If not, the next step is step 363. If so, the next step is step 364.

In step 363, the trust region is contracted, i.e., its volume is reduced. This can be done by shrinking the region uniformly or by removing a certain subvolume from the region. In this case, the result of decision step 360 is that the controller determines that the next point y does not satisfy the selected convergence criteria, regardless of what those criteria are. Moving from x to y would move the value of $f$ farther from the extremum. This indicates approximation error is dominating the computation, so the size of the trust region is reduced. Moreover, the next step is step 320 ("DO NOT UPDATE" shown in FIG. 3A). Since an improvement was not found, the process is repeated from the same point, but with a smaller trust region, in hopes that an improvement can be found close to x.

In step 364, since $f(y)$ is closer to the extremum than $f(x)$, the controller determines whether the next point in fact satisfies the selected convergence criteria. If so, a sufficiently accurate approximation of the extremum has been located and the method is complete. If not, in step 365, the trust region is expanded (increased in volume) and the controller determines y did not satisfy the convergence criteria. The next step is step 370 ("UPDATE" shown in FIG. 3A). Since an improvement was found, the next iteration starts from y rather than x (step 370).

In various aspects, before step 363 or step 364, in step 366, the controller computes a confidence 367 in the estimate. The confidence is correlated with the difference between the computed $f(y)$ and the value at y based on the quadratic estimate. The trust region can be expanded or contracted based on the computed confidence (indicated by the dotted arrows connecting confidence value 367 to steps 363, 364). The amount of contraction can be correlated with how much the confidence is below a selected confidence limit. Examples of confidence limits are described in Fletcher, R. *Practical Methods of Optimization, second edition*. Chichester: John Wiley, 1987; and in Nocedal, J. and Wright, S. J. *Numerical Optimization*. New York: Springer-Verlag, 1999. Examples are also given in Geyer, C. "Non-Linear Optimization," 2005, which is incorporated herein by reference.

Figure 3C:
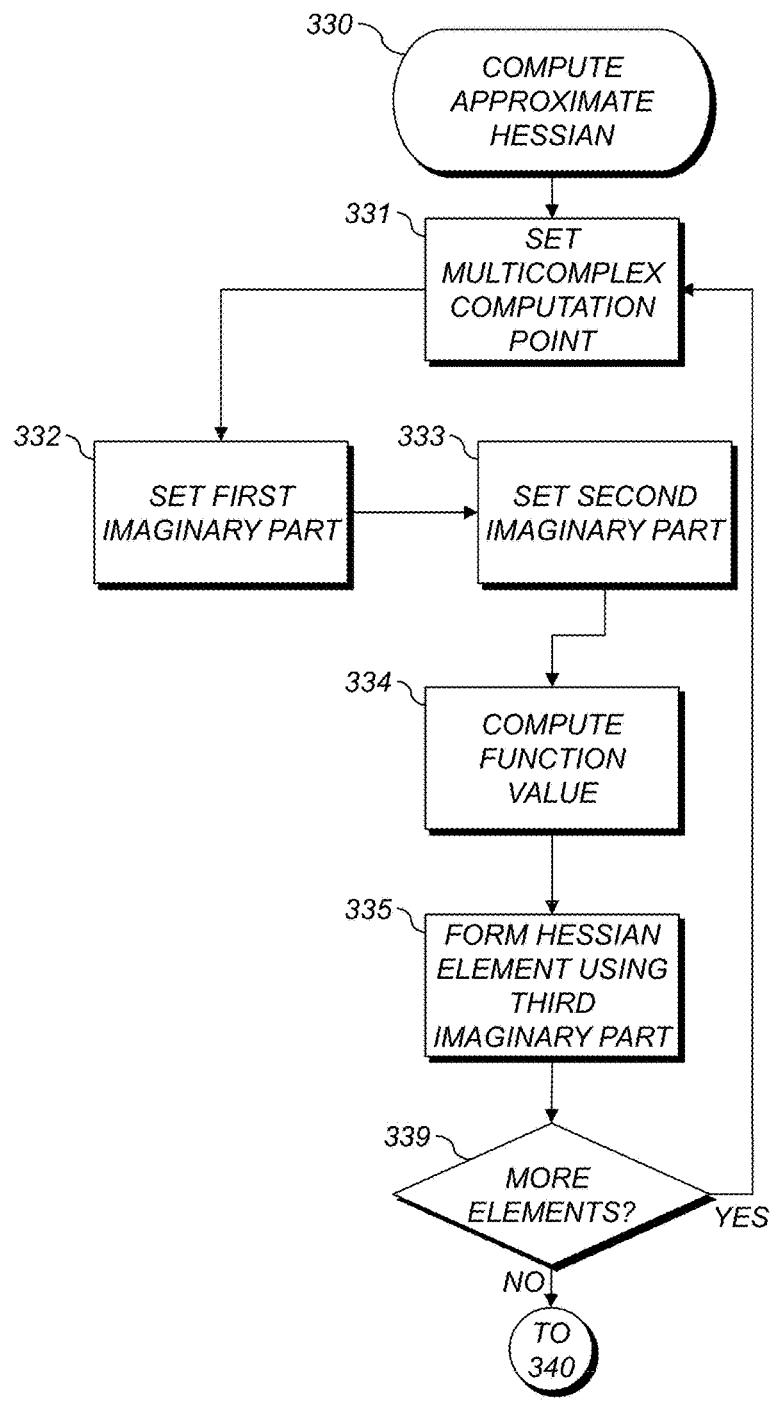
Figure 3D:
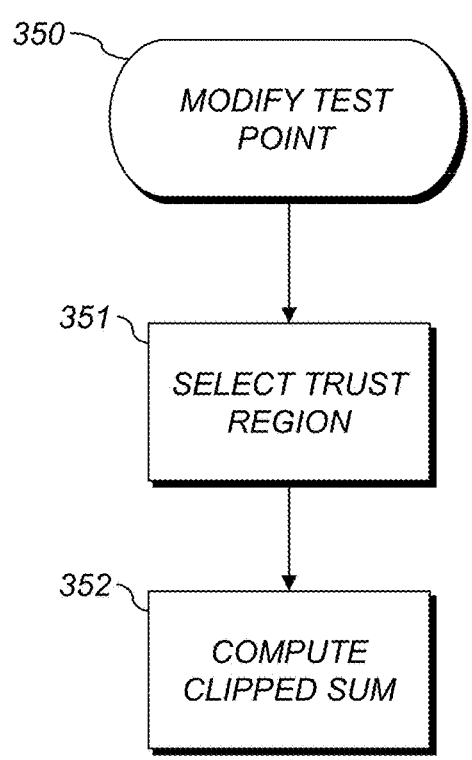
Figure 3E:
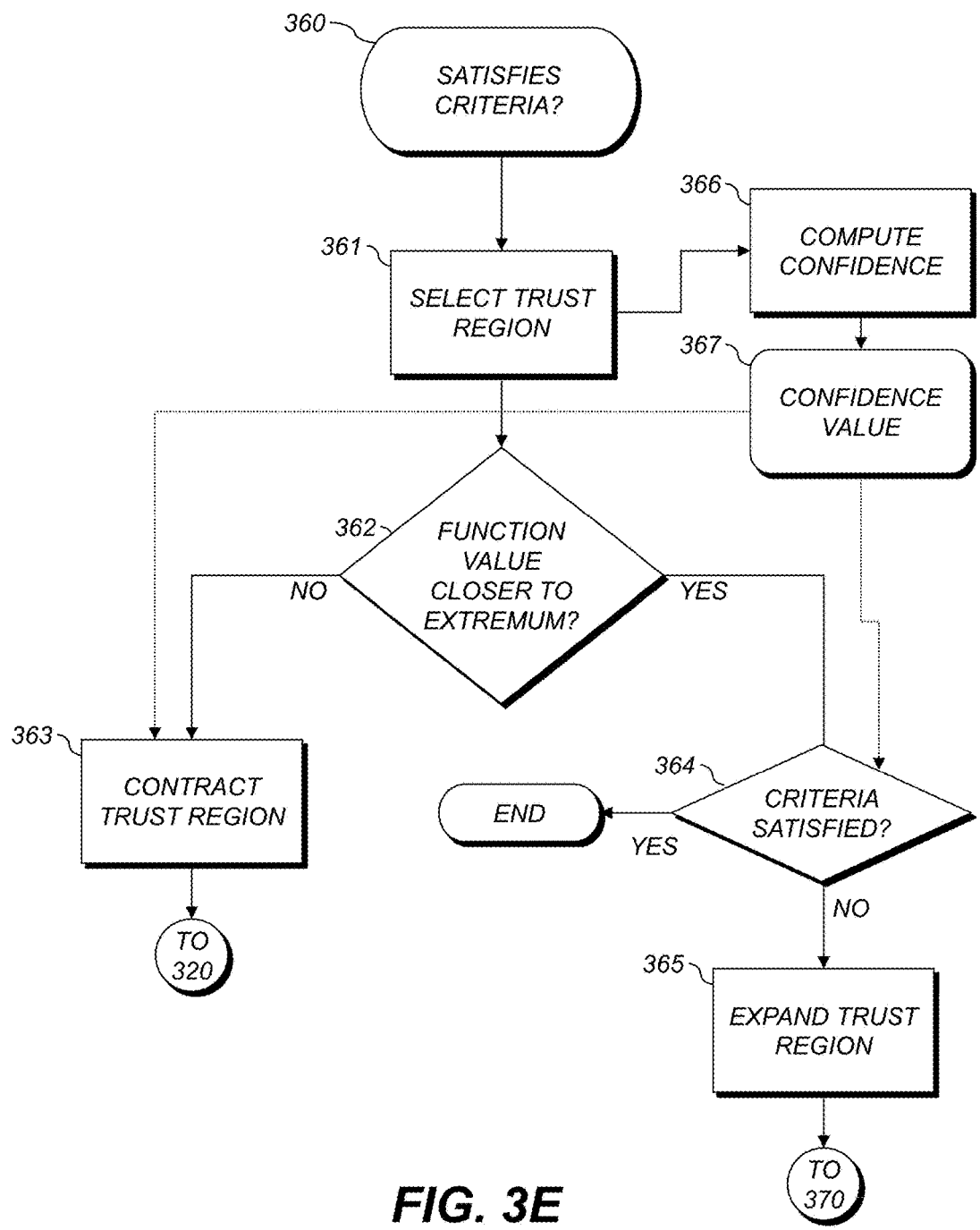
Figure 4:
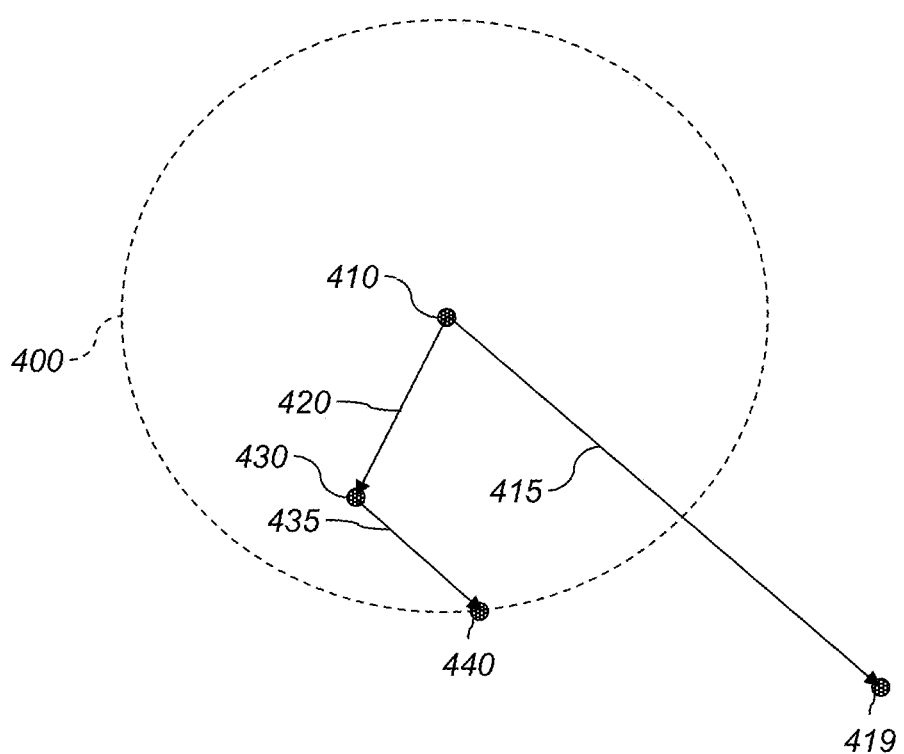
FIG. 4 shows an example of a dog-leg step.

In at least one embodiment, clipping step 351 discussed above includes determining a local minimum extending in a gradient direction from the test point using the computed approximate Jacobian. This is shown in FIG. 4. The controller determines the clipped sum to be the point at the intersection of the boundary of the trust region with the ray starting at the determined local minimum and extending parallel to the ray from the test point to the next point. This is known as a "dog-leg" step. The gradient direction is indicated by the computed approximate Jacobian, since the Jacobian is a vector pointing in the direction of greatest increase of $f$ at x by the definition of the derivative, gradient, and Jacobian. Therefore by following the line from x in the direction indicated by the Jacobian g (for maximizing; opposite g for minimizing), e.g., using Armijo-Goldstein line search, the controller finds a local extremum within the trust region. From the local extremum, the controller moves parallel to s until reaching the boundary of the trust region. The controller selects the resulting point as the next point y and proceeds to step 360 (FIG. 3).

FIG. 4 shows an example of a dog-leg step in a system with n=2, e.g., w=$f$(u,v). The figure shows the (u,v) plane. Test point 410 plus delta 415 would yield next point 419, which is beyond the boundary (dashed) of trust region 400. Therefore, the controller determines a local extremum 430 along a line segment 420 extending from the test point 410 in a direction indicated by the computed approximate Jacobian (either the direction of the Jacobian, or the opposite) to the boundary of the test region 400. The controller then determines the clipped sum, i.e., next point y, to be the point 440 at the intersection of the boundary of the trust region 400 with the ray 435 starting at the determined local extremum 430 and extending parallel to the ray 415 from the test point 410 to the next point 419.

Figure 5A:
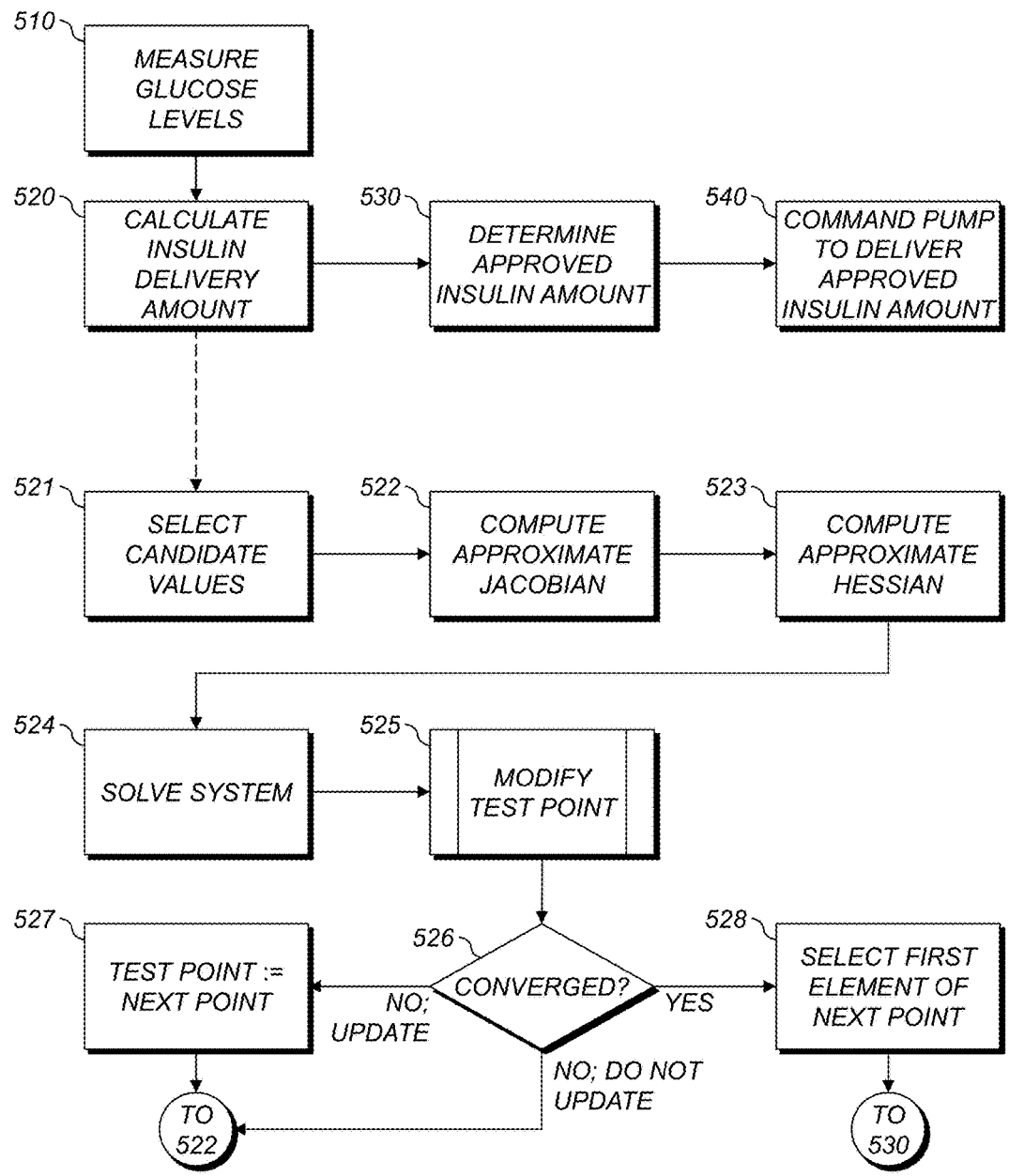
FIGS. 5A-5C are a flowchart illustrating exemplary methods of controlling an infusion pump.
Figure 5B:
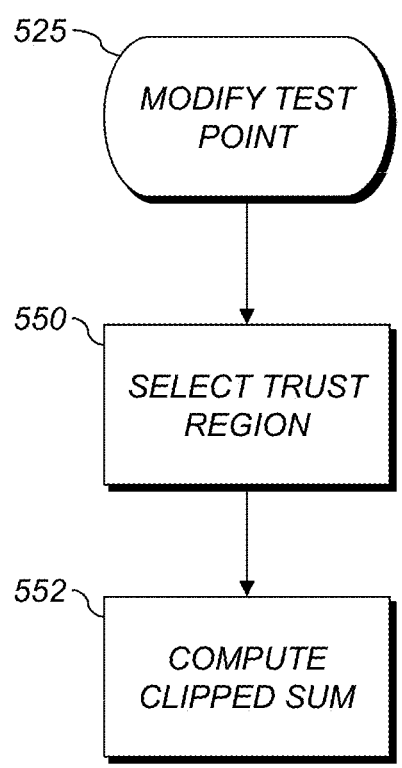
Figure 5C:
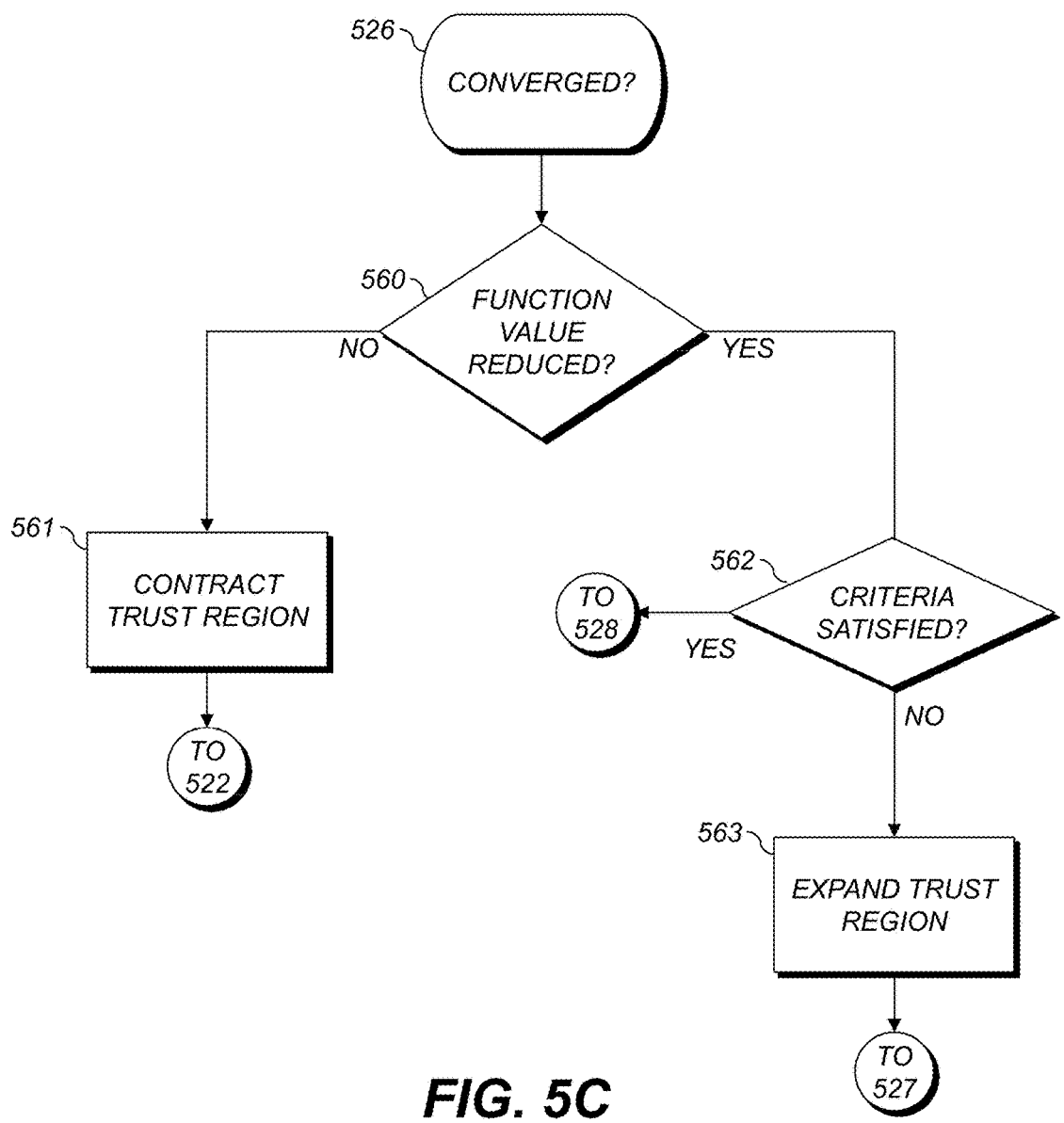

FIGS. 5A-5C are a flowchart illustrating exemplary methods of controlling an infusion pump. Solid arrows connect subsequent steps and dashed arrows connect steps to their substeps. The infusion pump (e.g., insulin pump 16, FIG. 2) is responsive to a controller (e.g., controller 10, FIG. 2) that receives data from at least one glucose sensor (e.g., glucose sensor 22). In various embodiments, the steps of the method are automatically performed using the controller. Processing begins with step 510.

In step 510, respective glucose levels of a physiological fluid from a subject are measured for each time interval of a series of discrete time intervals using the glucose sensor. The controller can receive from the glucose sensor one or more respective glucose level measurements for the measurement in each time interval of the series. The measurements can be measurements of a patient or subject, e.g., a human. The time intervals can be evenly spaced or not, and can skip in the middle. Step 510 is followed by step 520.

In step 520, using the controller, an insulin delivery amount for a selected one of the time intervals is automatically calculated. In an example, this is done using a model predictive controller. The model predictive controller, e.g., as discussed above, predicts an excursion of the glucose level from a selected target glucose range (e.g., $G^{zone}(k+j)$) using at least some of the glucose measurements, and optionally using estimates of a metabolic state of the subject. The model predictive controller then computes an estimated insulin delivery amount (e.g., $I_D$). In various examples, determining the estimated insulin delivery amount includes making an initial guess of $I_D$:=basal, as discussed above. The model predictive controller then adjusts the estimated insulin delivery amount, e.g., by mathematical minimization of J, to provide the candidate insulin delivery amount.

Determining the insulin delivery amount involves mathematically minimizing a cost function, as discussed herein (e.g., cost function J). The cost function computes a cost metric correlated with physiological-fluid glucose-level excursions from a selected target glucose range for a particular set of n successive candidate insulin delivery amounts beginning from the selected one of the time intervals. In an example, the n candidate insulin delivery levels are k, k+1, . . . , k+M−1, as discussed above. Step 520 includes substeps 521, 522, 523, 524, and 525, decision step 526, and steps 527 and 528.

Still referring to FIG. 5A, in step 521, n candidate insulin delivery values are selected for a real-type n-dimensional test point x. The values can be distinct or not, and can be, e.g., all zero.

In step 522, an approximate Jacobian g of the cost function (e.g., J) is computed at the test point. This can be done as evaluating the cost function, e.g., as described above with reference to step 320 (FIGS. 3A, 3B). For example, the model predictive controller can compute the cost function for each input set of n successive candidate insulin delivery amounts by predicting an excursion of the glucose level from a selected target glucose range using at least some of the glucose measurements, a glucose-insulin dynamic model of the subject, and the candidate insulin delivery amounts. This is the glucose-related cost (the Q term in Eq. 3, above). The controller can compute a deviation of the candidate insulin delivery amounts from respective selected basal delivery amounts, which can be the same as each other or different from each other. This is the deviation-related cost (the R term in Eq. 3, above). The controller can then form a weighted sum of respective values representing the predicted excursion and the computed deviation using respective selected weights such that the output of the cost function is or includes the weighted sum.

In step 523, an approximate Hessian H of the function is computed at the test point x. This can be done as described above with reference to step 330 (FIGS. 3A, 3C). Computation of the cost function can be done as described above with reference to step 326 (FIG. 3B) or step 335 (FIG. 3C). This is done using a multicomplex number; either bicomplex numbers or quaternions can be used.

In step 524, a system of equations defined by the approximate Hessian and the approximate Jacobian is solved to find a delta s. This can be done as described above with reference to step 340 (FIG. 3A). The system can be, e.g., Hs=−g. In an example, step 524 includes executing at least two iterations of a conjugate-gradient algorithm.

In step 525, the test point is modified according to the delta to form a next point y, e.g., y:=x+s. This can be done as described above with reference to step 350 (FIGS. 3A, 3D). Step 525 is followed by step 526. In various aspects, step 525 includes steps 550 and 552.

In step 550, a value is selected for a trust region, as discussed above (step 351, FIG. 3D). Step 550 is followed by step 552, in which the next point y is computed as the sum of the test point x and the delta s, and the sum is clipped within the trust region (as in step 352, FIG. 3D).

In decision step 526, the controller determines whether the next point y satisfies selected convergence criteria. This can be done as described above with reference to decision step 360 (FIGS. 3A, 3E). If not, the next step is step 527. If so, the next step is step 528. Also as discussed above, step 526 can include terminating the process if loop thresholds or tolerances have been met. In various aspects, decision step 526 includes steps 560, 561, 562, and 563.

In step 560, the controller determines whether the value of the function at the next point is lower than the value of the function at the test point. This is as discussed above with reference to step 362 of FIG. 3E. If not, the next step is step 561. If so, the next step is step 562.

In step 561, the controller contracts the trust region and determines that the next point does not satisfy the selected convergence criteria. The next step is step 522 ("DO NOT UPDATE" in FIG. 5A). As discussed above with reference to step 363 (FIG. 3E), the test point is not set to the next point because that would lead farther from the desired minimum.

In step 562, the controller determines whether the next point satisfies the selected convergence criteria. If so, the next step is step 528. If not, the next step is step 563, in which the trust region is expanded. Step 563 is followed by step 527 (FIG. 5A). The next point is used since it was an improvement, as discussed above with reference to step 365 (FIG. 3E).

In step 527, the value of the next point is assigned to the test point (x:=x+s) and the computing of the approximate Jacobian and Hessian, solving the system of equation, modifying the test point and determining are repeated. The next step is thus step 522.

In step 528, since next point y meets the convergence criteria, a first element of the next pointy is selected as the candidate insulin delivery amount for the selected one of the time intervals. E.g., for y=[$y_1$, $y_2$, . . . , $y_n$], $y_1$ is selected as $I'_D(k)$, the insulin to be delivered (specifically, the amount by which to adjust the basal insulin delivery for time interval k to determine the insulin amount $I_D(k)$ to deliver). Step 528 is followed by step 530.

In step 530, an approved insulin delivery amount is determined from the insulin delivery amount. In an example, the approved amount is set equal to the determined delivery amount. In another example, a safety module determines the approved amount. Specifically, in an example, the determined delivery amount is reduced according to a safety model, e.g., a hypoglycemia safety model, to provide the approved insulin delivery amount. The hypoglycemia safety model can be the glucose model used by the model predictive controller, or can be a different model. If the hypoglycemic safety model indicates the candidate insulin delivery amount will not lead to hypoglycemia, the determined insulin delivery amount is approved unchanged, i.e., with a reduction of zero (0). If the hypoglycemic safety model indicates the determined insulin delivery amount may lead to hypoglycemia, the determined insulin delivery amount is reduced to an amount that does not lead to hypoglycemia according to the hypoglycemic safety model. Step 530 is followed by step 540.

In step 540, the controller commands the infusion pump to deliver the approved insulin delivery amount. In this way, insulin can be delivered to a patient to maintain the patient's blood glucose within the desired glycemic zone.

In various examples, the computing-approximate Jacobian step 522 includes, for each dimension i of the n dimensions, setting a complex-type n-dimensional computation point c equal to the test point; setting an imaginary part of element i of c equal to a nonzero increment; computing a complex-type value of the cost function at c; and dividing the imaginary part of the complex-type computed function value by the increment to form element i of the Jacobian. This can be done as discussed above with reference to step 320 (FIGS. 3A, 3B).

In various examples, the computing-approximate-Hessian step 523 includes, for each pair of dimensions (i,j), each i and j one of the n dimensions, setting a bicomplex-type n-dimensional computation point b equal to the test point; setting a first imaginary part of element i of b equal to a nonzero first increment; setting a second imaginary part of element j of b equal to a nonzero second increment; computing a bicomplex-type value of the cost function at b; and dividing the combined imaginary part of the computed bicomplex-type function value by the product of the first and second increments to form element (i,j) of the Hessian. This can be done as described above with reference to step 330 (FIGS. 3A, 3C).

To recap, the system of FIG. 2 is provided to manage diabetes of a subject. In this system, the following components are utilized: continuous glucose sensor 22, pump 16, and controller 10. The continuous glucose monitor continuously measures glucose level of the subject at discrete generally uniform time intervals (indexed "k", e.g., approximately every 30 seconds or every minute, or every five minutes) and provides the glucose level at each interval in the form of glucose measurement data. The insulin infusion pump is controlled by the controller 10 to deliver insulin to the subject 20. The controller 10 is programmed with the appropriate MPC program to control the pump and communicate with the glucose meter and the glucose monitor. In this aspect, the controller determines an insulin delivery rate for each time interval in the time interval index (k) from the model predictive control based on desired glucose concentration 12 and glucose concentration 24 measured by the monitor 22 at each interval of the interval index (k).

FIG. 6 shows various embodiments of apparatus for the delivery of insulin, including data-processing components for analyzing data and performing other analyses and functions described herein, and related components. Subject 1138 is not part of the apparatus but is shown for context. Glucose monitor 1121 is adapted to measure respective glucose levels of subject 1138 at discrete time intervals, e.g., continually or intermittently, and provide respective glucose measurement data indicating each measured glucose level. Glucose monitor 1121 can include one or more glucose sensor(s) 1122, e.g., including glucose oxidase or glucose dehydrogenase, to transduce glucose concentration to a signal that can be measured electrochemically. Examples of glucose sensors are discussed above. Insulin infusion pump 1125 is configured to deliver insulin, e.g., to subject 1138, in response to a delivery control signal. The apparatus includes a controller, e.g., data processing system 1110, that receives glucose measurement data from the glucose monitor 1121 and commands the pump 1125 to deliver insulin.

A peripheral system 1120, a user interface system 1130, and a data storage system 1140 are communicatively connected to the data processing system 1110. Data processing system 1110 can be communicatively connected to network 1150, e.g., the Internet or an X.25 network, as discussed below.

The data processing system 1110 includes one or more data processor(s) that implement processes of various aspects described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 1120, user interface system 1130, and data storage system 1140 are shown separately from the data processing system 1110 but can be stored completely or partially within the data processing system 1110.

The data storage system 1140 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to the data processing system 1110 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 1110 to perform a particular series of operational steps when loaded, thereby implementing functions or acts specified herein.

In an example, data storage system 1140 includes memory 1141, e.g., a random-access memory, and disk 1142, e.g., a tangible computer-readable storage device such as a hard drive or a solid-state flash drive. Computer program instructions are read into memory 1141 from disk 1142, or a wireless, wired, optical fiber, or other connection. Data processing system 1110 then executes one or more sequences of the computer program instructions loaded into memory 1141, as a result performing process steps described herein. In this way, data processing system 1110 carries out a computer implemented process that provides for a technical effect of controlling insulin output based on inputs to a model of a biological system. For example, blocks of the flowchart illustrations or block diagrams herein, and combinations of those, can be implemented by computer program instructions. Memory 1141 can also store data used by running programs. In this example, memory 1141 (or other components in data storage system 1140) stores an insulin delivery profile including a plurality of basal insulin delivery amounts at respective ones of the discrete time intervals.

Computer program code can be written in any combination of one or more programming languages, e.g., Java, Smalltalk, C++, C, or an appropriate assembly language. Program code to carry out methods described herein can execute entirely on a single data processing system 1110 or on multiple communicatively-connected data processing systems 1110. For example, code can execute wholly or partly on a user's computer and wholly or partly on a remote computer, e.g., a server. The remote computer can be connected to the user's computer through network 1150. The user's computer or the remote computer can be non-portable computers, such as conventional desktop personal computers (PCs), or can be portable computers such as tablets, cellular telephones, smartphones, or laptops.

The peripheral system 1120 can include one or more devices configured to provide digital content records or other data to the data processing system 1110. In this example, glucose monitor 1121 (with glucose sensor(s) 1122) and glucose pump 1125 are connected to data processing system 1110 via peripheral system 1120. The monitor 1121 and the pump 1125 can also be directly connected to data processing system 1110. The peripheral system 1120 can also include digital still cameras, digital video cameras, cellular phones, or other data processors. The peripheral system 1120 can also include one or more bus bridge(s), e.g., to operatively connect devices having USB, FIREWIRE, RS-232, or other interfaces to data processing system 1110. The data processing system 1110, upon receipt of data from a device in the peripheral system 1120, can store that data in the data storage system 1140.

Data processing system 1110 is communicatively connected to interface 1131, which can include user interface system 1130 or network 1150. For example, the interface 1131 can include one or more touchscreen(s), button(s), switch(es), or network connection(s). Interface 1131 selectively receives a temporary insulin delivery profile extending over a selected time range of the time intervals and provides a first signal to data processing system 1110 indicating whether the temporary insulin delivery profile was received. This signal can be a flag set in memory in data storage system 1140 or a specific logic level or voltage on a wire or other electrical connection between interface 1131 and data processing system 1110. The signal can indicate whether or not the temporary insulin delivery profile was received using respective, different values of the signal (e.g., logic low or logic high) or by the presence or absence of the signal (e.g., a pulse is transmitted when the profile is received, so if no pulse has been transmitted, the profile has not been received). In at least one embodiment, the interface 1131 can be operated by the subject 1138, as represented graphically by the dashed line.

The user interface system 1130 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, or any device or combination of devices from which data is input to the data processing system 1110. In this regard, although the peripheral system 1120 is shown separately from the user interface system 1130, the peripheral system 1120 can be included as part of the user interface system 1130.

The user interface system 1130 also can include a display device, a processor-accessible memory, or any device or combination of devices to which data is output by the data processing system 1110. In this regard, if the user interface system 1130 includes a processor-accessible memory, such memory can be part of the data storage system 1140 even though the user interface system 1130 and the data storage system 1140 are shown separately in FIG. 6.

In various aspects, interface 1131 includes communication interface 1115 that is coupled via network link 1116 to network 1150. For example, communication interface 1115 can be an integrated services digital network (ISDN) card or a modem to provide a data communication connection to a corresponding type of telephone line. As another example, communication interface 1115 can be a network card to provide a data communication connection to a compatible local-area network (LAN), e.g., an Ethernet LAN, or wide-area network (WAN). Wireless links, e.g., WiFi or GSM, can also be used. Communication interface 1115 sends and receives electrical, electromagnetic or optical signals that carry digital data streams representing various types of information across network link 1116 to network 1150. Network link 1116 can be connected to network 1150 via a switch, gateway, hub, router, or other networking device.

Network link 1116 can provide data communication through one or more networks to other data devices. For example, network link 1116 can provide a connection through a local network to a host computer or to data equipment operated by an Internet Service Provider (ISP).

Data processing system 1110 can send messages and receive data, including program code, through network 1150, network link 1116 and communication interface 1115. For example, a server can store requested code for an application program (e.g., a JAVA applet) on a tangible non-volatile computer-readable storage medium to which it is connected. The server can retrieve the code from the medium and transmit it through the Internet, thence a local ISP, thence a local network, thence communication interface 1115. The received code can be executed by data processing system 1110 as it is received, or stored in data storage system 1140 for later execution.

The controller, e.g., data processing system 1110, is adapted to perform specific processing for each of a plurality of the discrete time intervals. Memory 1141 can store program instructions that cause data processing system 1110 to perform these processes. The data processing system 1110 receives the glucose measurement data for that time interval from the glucose monitor 1121 via the peripheral system 1120. The data processing system 1110 then determines an insulin delivery amount for that time interval using model predictive control based on a selected target glucose concentration range or zone (discussed above), the received glucose measurement data, and the stored basal insulin delivery profile amounts for that time interval and n−1 successive time intervals. This is discussed above with reference to step 520 (FIG. 5A). The data processing system 1110 then provides to the insulin infusion pump 1125 a delivery control signal corresponding to the determined insulin delivery amount. The insulin infusion pump 1125 then delivers a corresponding amount of insulin, e.g., to subject 1138.

The model predictive controller in or implemented by data processing system 1110 is adapted to determine the insulin delivery amount by mathematical minimization of a cost function that computes a cost metric correlated with physiological-fluid glucose-level excursions from a selected target glucose range for a particular set of n successive candidate insulin delivery amounts beginning from the selected one of the time intervals. The model predictive controller, in order to carry out the mathematical minimization, is adapted to select n candidate insulin delivery values for a real-type n-dimensional test point, as discussed above with reference to step 310 (FIG. 3A).

For each dimension i of the n dimensions, the controller is adapted to set a complex-type n-dimensional computation point c equal to the test point (step 322, FIG. 3B); set an imaginary part of element i of c equal to a nonzero increment (step 324, FIG. 3B); compute a complex-type value of the cost function at c (step 326, FIG. 3B); and divide the imaginary part of the complex-type computed function value by the increment to form element i of an approximate Jacobian g of the function at the test point (step 328, FIG. 3B).

For each pair of dimensions (i,j), each i and j one of the n dimensions, the controller is programmed or otherwise adapted to set a multicomplex-type n-dimensional computation point b equal to the test point (step 331, FIG. 3C). For example, the data processing system 1110 can be programmed to store and manipulate records or arrays holding four floating-point values for each of the n dimensions. These records or arrays can be loaded with appropriate values (e.g., in MATLAB, b=zeros (n, 4); b(:,1)=x). The multicomplex type can be a bicomplex type and the first, second, and third imaginary parts can be first, second, and combined imaginary parts for bases $i_1$, $i_2$, $i_1 i_2$, respectively, as described above. The multicomplex type can alternatively be a quaternion type, and the first, second, and third imaginary parts can be $i_Q$, $j_Q$, and $k_Q$ parts, respectively. The controller is adapted to set a first imaginary part of element i of b equal to a nonzero first increment (step 332, FIG. 3C; e.g., b (i,2)=delta1); set a second imaginary part of element j of b equal to a nonzero second increment (step 333, FIG. 3C; e.g., b (j,3)=delta2); compute a multicomplex-type value v of the cost function at b (step 334, FIG. 3C); and divide the third imaginary part of the computed multicomplex-type function value by the product of the first and second increments to form element (i, j) of an approximate Hessian H of the function at the test point (step 335, FIG. 3C; e.g., $$H(i,j)=v(4)/(\text{delta1}*\text{delta2})).$$

The controller is further adapted to solve a system of equations defined by the approximate Hessian and the approximate Jacobian, e.g., Hs=−g, to find a delta s (step 340, FIG. 3A); modify the test point according to the delta to form a next point (step 350, FIGS. 3A, 3D); determine whether the next point satisfies selected convergence criteria (step 360; FIGS. 3A, 3E); if not, assign the value of the next point to the test point and repeat the computation of the approximate Jacobian and Hessian of the function, solution of the system of equations, modification of the test point, and determination of whether the next point satisfies the selected convergence criteria (FIG. 3A); and if so, select the first element of the next point as the candidate insulin delivery amount for the selected one of the time intervals (see discussion of step 364, FIG. 3E).

In order to compute the cost function for each input set of n successive candidate insulin delivery amounts (ID'guess), the model predictive controller is adapted to predict an excursion of the glucose level from a selected target glucose range using at least some of the glucose measurements, a glucose-insulin dynamic model of the subject, and an input set of n candidate insulin delivery amounts (G'(k), Eq. 2 above); to compute a deviation of the candidate insulin delivery amounts from respective selected basal delivery amounts. This was discussed above; see Eq. 3 and the discussion of step 522 (FIG. 5A). The controller is also adapted to form a weighted sum of respective values representing the predicted excursion and the computed deviation using respective selected weights (Eq. 3 factors Q and R, which can be the same or different, and can both be 1.0), such that the output of the cost function includes the weighted sum.

In some embodiments, the data processing system 1110, a model predictive controller therein, a safety subsystem thereof, or a safety component attached thereto, is programmed to predict an excursion of a glucose level of the subject 1138 from the selected target glucose range. This is done using a hypoglycemia safety model and at least some of the glucose measurement data for a plurality of the time intervals. The system or component then reduces the determined insulin delivery amount according to the predicted excursion.

In view of the foregoing, embodiments of the invention provide improved control of insulin delivery amounts in glucose pumping systems. Various features described herein provide ways of more efficiently performing MPC computations (e.g., computing Jacobians and Hessians) that can be implemented on low-powered portable or mobile electronic devices. A technical effect of computation of Jacobians using complex numbers, and of computation of Hessians using multicomplex numbers, is to permit more frequent changes in pump operation so that the controller/pump system responds more quickly to changes in blood glucose level. Moreover, these computations provide reduced round-off error, a technical effect of which is that the amount of insulin delivered will more accurately follow the glucose model and can thus reduce the probability of mis-dosing of insulin due to round-off error.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. Apparatus for the delivery of insulin, the apparatus comprising:
   a) a glucose monitor adapted to measure respective glucose levels of a subject at discrete time intervals and provide respective glucose measurement data indicating each measured glucose level;
   b) an insulin infusion pump configured to deliver insulin in response to a delivery control signal;
   c) a memory configured to store a plurality of basal insulin delivery amounts at respective ones of the discrete time intervals; and
   d) a model predictive controller adapted to, for each of a plurality of the discrete time intervals:
      i) receive the glucose measurement data for that time interval from the glucose monitor;
      ii) determine an insulin delivery amount for that time interval using model predictive control based on a selected target glucose concentration range, the received glucose measurement data, the stored basal insulin delivery profile amounts for that time interval and n−1 successive time intervals; and
      iii) provide to the insulin infusion pump a delivery control signal corresponding to the determined insulin delivery amount, so that a corresponding amount of insulin is delivered by the infusion pump;
   e) in which the model predictive controller is adapted to determine the insulin delivery amount by mathematical minimization of a cost function that computes a cost metric correlated with physiological-fluid glucose-level excursions from a selected target glucose range for a particular set of n successive candidate insulin delivery amounts beginning from the selected one of the time intervals, and the model predictive controller, in order to carry out the mathematical minimization, is adapted to:
      i) select n candidate insulin delivery values for a real-type n-dimensional test point;
      ii) for each dimension i of the n dimensions:
         A) set a complex-type n-dimensional computation point c equal to the test point;
         B) set an imaginary part of element i of c equal to a nonzero increment;
         C) compute a complex-type value of the cost function at c; and
         D) divide the imaginary part of the complex-type computed function value by the increment to form element i of an approximate Jacobian of the function at the test point;
      iii) for each pair of dimensions (i,j), each i and j one of the n dimensions:
         A) set a multicomplex-type n-dimensional computation point b equal to the test point;
         B) set a first imaginary part of element i of b equal to a nonzero first increment;
         C) set a second imaginary part of element j of b equal to a nonzero second increment;
         D) compute a multicomplex-type value of the cost function at b; and
         E) divide the third imaginary part of the computed multicomplex-type function value by the product of the first and second increments to form element (i,j) of an approximate Hessian of the function at the test point;
      iv) solve a system of equations defined by the approximate Hessian and the approximate Jacobian to find a delta;
      v) modify the test point according to the delta to form a next point;
      vi) determine whether the next point satisfies selected convergence criteria;
      vii) if not, assign the value of the next point to the test point and repeat the computation of the approximate Jacobian and Hessian of the function, solution of the system of equations, modification of the test point, and determination of whether the next point satisfies the selected convergence criteria; and
      viii) if so, select the first element of the next point as the candidate insulin delivery amount for the selected one of the time intervals;

f) and further in which the model predictive controller is adapted to, in order to compute the cost function for each input set of n successive candidate insulin delivery amounts:
  i) predict an excursion of the glucose level from a selected target glucose range using at least some of the glucose measurements, a glucose-insulin dynamic model of the subject, and an input set of n candidate insulin delivery amounts;
  ii) compute a deviation of the candidate insulin delivery amounts from respective selected basal delivery amounts; and
  iii) form a weighted sum of respective values representing the predicted excursion and the computed deviation using respective selected weights, such that the output of the cost function includes the weighted sum; and
g) deliver, with the insulin infusion pump, the determined insulin delivery amount of insulin to the subject, as provided by the delivery control signal from the controller.

2. The apparatus according to claim 1, wherein the model predictive controller is further adapted to:
  a) predict an excursion of a glucose level of the subject from the selected target glucose range using a safety model and at least some of the glucose measurement data for a plurality of the time intervals; and
  b) reduce the determined insulin delivery amount according to the predicted excursion.

3. The apparatus according to claim 1, wherein the glucose monitor includes a plurality of glucose sensors.

4. The apparatus according to claim 1, wherein the multicomplex type is a bicomplex type and the third imaginary part is a combined imaginary part.

5. The apparatus according to claim 1, wherein the multicomplex type is a quaternion type, and the first, second, and third imaginary parts are $i_Q$, $j_Q$, and $k_Q$ parts, respectively.

6. A method to control an infusion pump responsive to a controller that receives data from a glucose sensor, the method comprising:
  a) measuring respective glucose levels of a physiological fluid from a subject for each time interval of a series of discrete time intervals using the glucose sensor; and
  b) using a controller, automatically calculating an insulin delivery amount for a selected one of the time intervals by mathematically minimizing a cost function that computes a cost metric correlated with physiological-fluid glucose-level excursions from a selected target glucose range for a particular set of n successive candidate insulin delivery amounts beginning from the selected one of the time intervals, the minimizing including:
    i) selecting n candidate insulin delivery values for a real-type n-dimensional test point;
    ii) computing an approximate Jacobian of the cost function at the test point by evaluating the cost function, in which the model predictive controller computes the cost function for each input set of n successive candidate insulin delivery amounts by:
      A) predicting an excursion of the glucose level from a selected target glucose range using at least some of the glucose measurements, a glucose-insulin dynamic model of the subject, and the candidate insulin delivery amounts;
      B) computing a deviation of the candidate insulin delivery amounts from respective selected basal delivery amounts; and
      C) forming a weighted sum of respective values representing the predicted excursion and the computed deviation using respective selected weights such that the output of the cost function includes the weighted sum;
    iii) computing an approximate Hessian of the cost function at the test point by evaluating the cost function;
    iv) solving a system of equations defined by the approximate Hessian and the approximate Jacobian to find a delta;
    v) modifying the test point according to the delta to form a next point;
    vi) determining whether the next point satisfies selected convergence criteria;
    vii) if not, assigning the value of the next point to the test point and repeating the computing of the approximate Jacobian and Hessian, solving the system of equation, modifying the test point and the determining step; and
    viii) if so, selecting a first element of the next point as the candidate insulin delivery amount for the selected one of the time intervals;
  (c) commanding, with a control signal from the controller, the infusion pump to deliver the calculated insulin delivery amount to the subject; and
  d) delivering, with the infusion pump, the calculated insulin delivery amount of insulin to the subject.

7. The method according to claim 6, in which:
a) the computing-approximate Jacobian step includes, for each dimension i of the n dimensions:
  i) setting a complex-type n-dimensional computation point c equal to the test point;
  ii) setting an imaginary part of element i of c equal to a nonzero increment;
  iii) computing a complex-type value of the cost function at c; and
  iv) dividing the imaginary part of the complex-type computed function value by the increment to form element i of the Jacobian; and
b) the computing-approximate-Hessian step includes, for each pair of dimensions (i,j), each i and j one of the n dimensions:
  i) setting a multicomplex-type n-dimensional computation point b equal to the test point;
  ii) setting a first imaginary part of element i of b equal to a nonzero first increment;
  iii) setting a second imaginary part of element j of b equal to a nonzero second increment;
  iv) computing a multicomplex-type value of the cost function at b; and
  v) dividing the third imaginary part of the computed multicomplex-type function value by the product of the first and second increments to form element (i,j) of the Hessian.

8. The method according to claim 7, wherein the multicomplex type is a bicomplex type and the third imaginary part is a combined imaginary part.

9. The method according to claim 7, wherein the multicomplex type is a quaternion type, and the first, second, and third imaginary parts are $i_Q$, $j_Q$, and $k_Q$ parts, respectively.

10. The method according to claim 6, wherein the determining-approved-amount step includes providing the candidate insulin delivery amount as the approved insulin delivery amount.

11. The method according to claim 6, wherein the determining-approved-amount step includes reducing the candidate delivery amount according to a safety model to provide the approved insulin delivery amount.

12. The method according to claim 6, wherein the solving step includes executing at least two iterations of a conjugate-gradient algorithm.

13. The method according to claim 6, further including selecting a value for a trust region, in which the modifying step includes computing the next point as the sum of the test point and the delta and clipping the sum within the trust region, and the determining step includes:
  a) determining whether the value of the function at the next point is lower than the value of the function at the test point;
  b) if not, contracting the trust region and determining that the next point does not satisfy the selected convergence criteria; and
  c) if so, determining whether the next point satisfies the selected convergence criteria and, if not, expanding the trust region.

* * * * *